United States Patent [19]
Perez et al.

[11] Patent Number: 5,852,049
[45] Date of Patent: Dec. 22, 1998

[54] AROMATIC ETHERS DERIVED FROM INDOLES WHICH ARE USEFUL AS MEDICAMENTS

[75] Inventors: Michel Perez, Castres; Serge Halazy, Lagarrigue; Gareth John, Les Salvages; Jean-Pierre Valentin, Catanet-Tolosan; Peter Pauwels, Lautrec, all of France

[73] Assignee: Pierre Fabre Medicament, Boulogne, France

[21] Appl. No.: 809,028

[22] PCT Filed: Sep. 22, 1995

[86] PCT No.: PCT/FR95/01220

§ 371 Date: Mar. 21, 1997

§ 102(e) Date: Mar. 21, 1997

[87] PCT Pub. No.: WO96/09288

PCT Pub. Date: Mar. 28, 1996

[30] Foreign Application Priority Data

Sep. 22, 1994 [FR] France .................... 94 11305

[51] Int. Cl.⁶ .................. A61K 31/40; C07D 209/16
[52] U.S. Cl. .................. 514/415; 514/419; 548/504; 548/506
[58] Field of Search .................. 548/504, 506; 514/415, 419

[56] References Cited

FOREIGN PATENT DOCUMENTS

| | | |
|---|---|---|
| 93/11106 | 6/1993 | WIPO . |
| 94/14770 | 7/1994 | WIPO . |
| 94/15916 | 7/1994 | WIPO . |
| 95/01334 | 1/1995 | WIPO . |
| 95/06638 | 3/1995 | WIPO . |

OTHER PUBLICATIONS

Glennon, Richard A. et al., Drug Dev. Res., vol. 22, No. 1, pp. 25–36 (1991).

Glennon et al., Chemical Abstracts, 114:178477 (1991).

Gordeev et al., Chemical Abstracts, 118:233816 (1993).

*Primary Examiner*—Fiona T. Powers
*Attorney, Agent, or Firm*—Rockey, Milnamow & Katz, Ltd.

[57] ABSTRACT

The present invention relates to new aromatic ethers derived from indole and having general formula (I) as well as to their preparation methods, pharmaceutical compositions containing them and their utilization as a medicament for the treatment of diseases linked to the dysfunction of the $5HT_1$-like receptors.

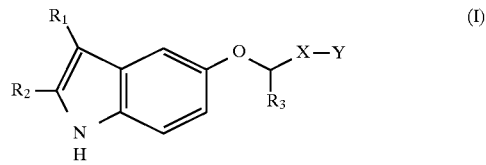

28 Claims, No Drawings

AROMATIC ETHERS DERIVED FROM INDOLES WHICH ARE USEFUL AS MEDICAMENTS

This application is a 371 of PCT/FR95/01220 field Sep. 22, 1995.

The present invention relates to new aromatic ethers derived from indols, as well as the processes for preparing them, the pharmaceutical compositions containing them and their use as medicaments.

Serotonin or 5-hydroxytryptamine (5HT) plays an important role both at the level of the nervous system and at the level of the cardiovascular system and serotoninergic receptors have been identified either at the central or peripheral level. It is generally accepted that serotonin may play an important role in various types of pathological conditions such as certain psychiatric disorders (anxiety, depression, aggressiveness, panic attacks, obsessive compulsive disorders, schizophrenia, suicidal tendency), certain neurodegenerative disorders (Alzheimer's disease, Parkinsonism), migraine, cephalalgia and disorders linked to alcoholism (cf. E. Zifa and G. Fillion, Pharm. Reviews, 44, 401, 1992; A. Moulignier, Rev. Neuro. (Paris) 150, 3–15, 1994; S. Langer, N. Brunello, G. Racagni, J. Mendlecvicz, "Serotinin receptors subtypes: pharmacological significance and clinical implications" Karger ed.; 1992; B. E. Leonard, Int. Clin. Psychopharmacology, 7, 13–21, 1992; D. G. Grahame-Smith, Int. Clin. Psychopharmacology, 6, Suppl. 4, 6–13, 1992; E. Zifa, G. Fillion, Pharmacological Reviews, 44, 401–458, 1992; R. W. Fuller, J. Clin. Psychiatry, 53, 36–45, 1992).

The compounds according to the present invention are new compounds having a very high affinity and a very good selectivity for the receptors commonly called $5HT_{1-like}$ and more particularly for the receptors called $5HT_{1B}$ and $5HT_{1D}$, according to the new nomenclature recently proposed by P. Humphrey, P. Hartig and D. Hoyer (TIPS, 14, 233–236, 1993).

The medicaments including (alone or in combination with other therapeutic agents) the active ingredients of the present invention find use in the treatment, both curative and preventive, of diseases linked to the dysfunction of the $5HT_{1-like}$ receptors including the $5HT_{1B}$, $5HT_{1D\alpha}$ and $5HT_{1D\beta}$ receptors, to their deregulation or to modifications of the activity of the endogenous ligand (generally serotonin).

The compounds of the present invention are potent and selective ligands of the $5HT_{1-like}$ receptors which can act as agonists, partial agonists or antagonists at the level of these receptors, and may therefore find application in the above-mentioned disorders linked to serotonin.

Most of the compounds of the present invention are more particularly potent agonists (both at the level of their affinity and at the level of their intrinsic activity or efficacy) and selective agonists of the $5HT_{1B}$ and $5HT_{1D}$ receptors. The agonists of the $5HT_{1-like}$ receptors and more particularly of the $5HT_{1D}$ receptors exhibit a selective vasoconstrictive activity and find use in the treatment of migraine and vasospastic disorders [(see for example A. Doenicke et al., The Lancet, 1, 1309–1311, 1988; M. D. Ferrari, P. R. Saxena, Cephalalgia, 13, 151–165, 1993; S. J. Peroutka, Headache, 30, 5–11, 1990; M. A. Moskowitz, TiPS, 13, 307–311, 1992; W. Feniuk, P. P. Humphrey, M. S. Perren, H. E. Connor, E. T. Whalley, J. Neurol., 238, S57–S61, 1991; A. V. Deligonis, S. J. Peroutka, Headache, 31, 228–231, 1991)].

The compounds of the present invention which are, for the most part, potent and selective agonists of the $5HT_{1-like}$ receptors therefore find more particularly use in the curative and prophylactic treatment of "conventional" (with aura) or "common" (without aura) migraine attacks, vascular facial pain, chronic vascular cephalalgia and vasospastic disorders.

The prior state of the art in this domain is illustrated especially by:

Patent Applications EP-0,303,507-A2, WO 93/14087, WO 94/02460, WO 92/14708 and U.S. Pat. No. 4,839,377, GB 2,124,210A and GB 2,162,532A which describe sulfonamides derived from tryptamines (including sumatriptan) as antimigraine drugs.

Patent Applications GB 2,191,488A, GB 2,185,020A and GB 2,168,347A which describe alkylamides derived from tryptamine.

French Patent Applications F 9,215,919 (30/12/92) and F 9,307,982 (30/6/93) which describe new indole compounds derived from piperazines and arylamines respectively as ligands of the $5HT_{1B}$–$5HT_{1D}$ receptors.

Application for Patent of Invention FR 2,671,971 which describes 5-O-carboxymethylated derivatives of tryptamine which have a good affinity for the $5HT_{1D}$ receptors.

European Patent Applications 0,313,397, 0,486,666, 0,494,774-A1, 0,494,774, 0,497,512-A2, 0,501,568-A1, 0,464,558, 0,548,813-A1 and Patent Application WO 92/13856 and 93/11106 which describe heterocyclic derivatives derived from tryptamine as agonists of the $5HT_{1-like}$ receptors.

The present invention describes a new class of aromatic ethers derived from indole which differ from all the most closely related derivatives of the prior art in their original and different chemical structure, but also in their biological profile and their therapeutic potential since numerous compounds according to the present invention exhibit a very high affinity and selectivity for the "$5HT_{1-like}$" receptors and a remarkable agonist efficacy. These biological and pharmacological properties are particularly made evident when numerous derivatives of the present invention are compared with sumatriptan; the derivatives of the present invention therefore find, for the most part, more particularly their usefulness as active ingredients of medicinal compositions for the treatment of migraine and various similar disorders.

The present invention relates to the derivatives of general formula (I)

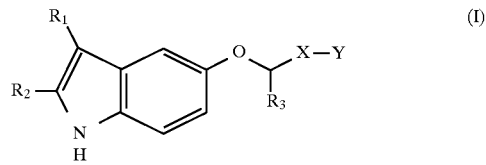

(I)

in which

R1 represents an amino residue corresponding to one of the formulae (i) to (vi):

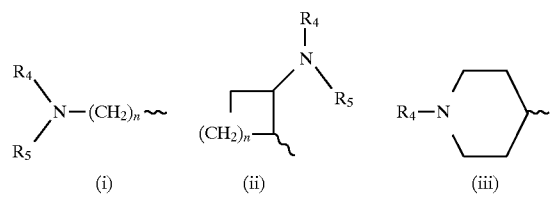

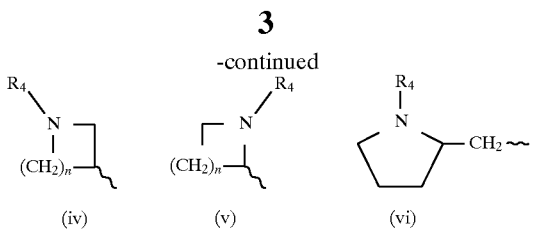

(iv)    (v)    (vi)

in which n represents an integer between 1 and 5.

R4 represents a hydrogen, a linear or branched alkyl group comprising from 1 to 6 carbon atoms or a residue of the $(CH_2)_mOR'$ type in which m represents an integer between 1 and 5, and R' a linear or branched alkyl group comprising from 1 to 6 carbon atoms.

R5 represents a hydrogen, or a linear or branched alkyl group comprising from 1 to 6 carbon atoms.

$R_2$ represents a hydrogen, or $R_1$ and $R_2$, taken together, form a ring with 6 carbon atoms substituted with an amine functional group $(NR_4R_5)$.

$R_3$ represents a hydrogen, an alkyl residue comprising from 1 to 5 carbon atoms or an aromatic residue such as a substituted phenyl.

X may be omitted or may represent either a linear or branched alkyl chain comprising from 1 to 8 carbon atoms or an aromatic residue such as a phenyl or heterocycle or alternatively an arylalkyl comprising from 1 to 10 carbon atoms which may be variously substituted at various positions with a linear or branched alkyl group comprising from 1 to 6 carbon atoms, an oxygen, an aryl, a halogen, an alcohol, an ether, an ester, a nitrile, a nitro, a ketone, a thiol, a thioether, an amine.

Y represents a carbonyl-containing $(COR_6)$, sulfonyl-containing $(SO_2R_6)$, oxygenated $(OR_7)$, amino $(NHR_8)$, nitrile (CN), nitro $(NO_2)$, oxime (C=NOH) or hydroxylamine (NHOH) residue in which $R_6$ represents $R'_6$, $OR'_6$ or $NHR''_6$ where $R'_6$ and $R''_6$ represent a linear or branched alkyl chain from 1 to 8 carbon atoms, a cycloalkyl from 4 to 10 carbon atoms, an aromatic residue such as a phenyl, a benzyl, or a phenethyl which are variously substituted, $R_7$ represents $R'_6$, $COR'_6$ or $COOR'_6$ or $CONHR'_6$ and $R_8$ represents a hydrogen or a residue such as $R''_6$, $COR'_6$, $CO_2R'_6$, $CONHR'_6$, $SO_2R'_6$ or $SO_2NR'_6R''_6$ with the following restrictions:

when Y represents $COR_6$, when X is omitted and when $R_3$ represents a hydrogen, then $R_1$ should be different from $CH_2CH_2N(R_4R_5)$, when $R''_6$ represents an aromatic residue, then $R_1$ should be different from $CH_2CH_2N(R_4R_5)$, and Y is different from an alkoxy group, their salts, hydrates, solvates and bioprecursors which are acceptable for therapeutic use.

The compounds of formula (I) containing 1 or more asymmetric centers have isomeric forms. The racemates and the pure enantiomers of these compounds also form part of this invention.

Among the salts which are acceptable for the therapeutic use of the indoles of general formula (I), there may be mentioned salts formed by addition with organic or inorganic acids and, for example, the hydrochlorides, hydrobromides, sulfates, fumarates and maleates. Other salts may be useful in the preparation of the compounds of formula (I), for example the adducts with creatinine sulfate.

The expression "bioprecursors" as used in the present invention applies to compounds whose structure differs from that of the compounds of formula (I), but which, when administered to an animal or to a human, are converted in the body to a compound of formula (I).

The compounds of the present invention are generally prepared by condensation of an indole derivative of general formula (II).

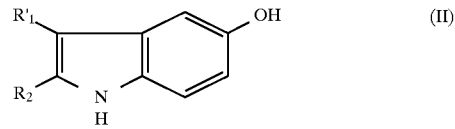

in which $R_2$ is defined as above and $R'_1$ may be equivalent to $R_1$ or to a precursor of $R_1$ (which will be restored at the end of the synthesis by an appropriate reaction such as for example the cutting of a protective group) with a derivative of general formula (III).

in which X, Y and $R_3$ are defined as above and L represent a leaving group such as a halogen (iodine, bromine or chlorine), a mesylate, a tosylate or a triflate.

The preparation of the derivatives of formula (I) by condensation of the derivatives of formula (II) with the derivatives of formula (III) may be carried out, in general, in the presence of an organic base (NaH, KH, $Et_3N$, DBU, DBN, TMP, DIPEA, $^tBuOK$) or an inorganic base ($K_2CO_3$, $KHCO_3$, $NaHCO_3$, $Cs_2CO_3$, KOH, NaOH, $CaCO_3$ and the like) in an anhydrous solvent such as THF, DMF, DMSO, acetone, diethyl ketone, methyl ethyl ketone, acetonitrile or DME at a temperature of between 20° and 140° C., in the presence or otherwise of a salt as catalyst and which may be KI, $Bu_4NI$, LiI, $AgBF_4$, $AgClO_4$, $Ag_2CO_3$, KF, $Bu_4NF$ or CsF. The choice of the experimental conditions and of the reagents for carrying out the condensation between the derivatives of formulae (II) and (III) to obtain the derivatives of formula (I) is quite obviously dependent on the nature of the substituents $R'_1$, $R_2$, X, Y, $R_3$ and L and will be made according to the methods and techniques well known to a person skilled in the art.

By way of example, some methods and variations are described below:

a. In the specific case of the derivatives of formula (I) in which $R_2$=H and $R_1$ represents $H_2N—CH_2—CH_2—$, a valuable method of preparation consists in condensing a serotonin derivative of formula (IIa)

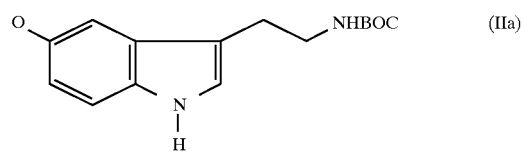

with an electrophile of formula (III) according to the methods and techniques described above, followed by deprotection of the N-t-butoxycarbonyl by reaction in acidic medium ($CF_3CO_2H$, HCl or $H_2SO_4$).

b. In the specific case of the derivatives of formula (Ib)

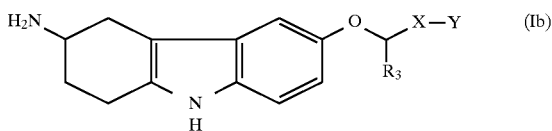
(Ib)

a valuable method of preparation consists in condensing an intermediate of formula (IIb)

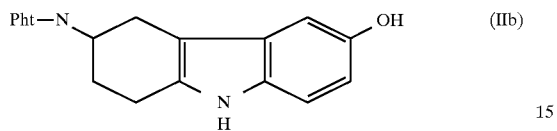
(IIb)

in which Pht represents a phthalimide, with an electrophile of formula (III) according to the methods and techniques described above, followed by deprotection of the phthalimide group by reaction with hydrazine or ethylenediamine. The intermediate of formula (IIb) (cf. J. Chem. Soc., No. 2, 325–326, 1970) is prepared by selective demethylation of an intermediate of structure (IV) with the aid of $BBr_3$.

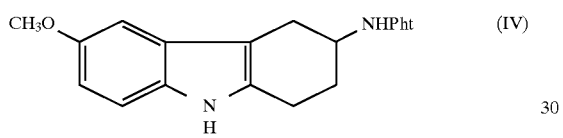
(IV)

c. In the specific case of the products of structure (Ic)

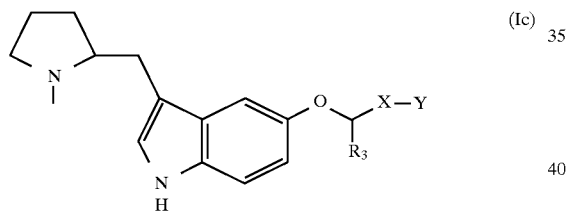
(Ic)

a very valuable method of preparation consists in condensing an intermediate of formula (IIc)

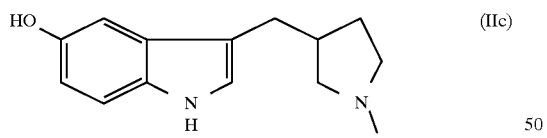
(IIc)

with an electrophile of structure (III) according to the methods and techniques described above. The intermediate of formula (IIc) is, for its part, prepared by selective O-demethylation with the aid of $BBr_3$ at low temperature from the methyl ether (V)

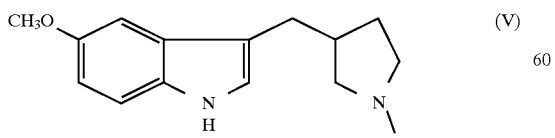
(V)

which is prepared according to the method described in J. Med. Chem. 35, 4503 (1992); the use of proline as starting product allows the enantioselective preparation of the R or S isomers of the intermediates (V) and (IIc) and consequently of each of these isomers at the level of the asymmetric carbon of the pyrrolidine ring in the final products of structures (Ic).

d. In the specific case of the compounds of general formula (Id)

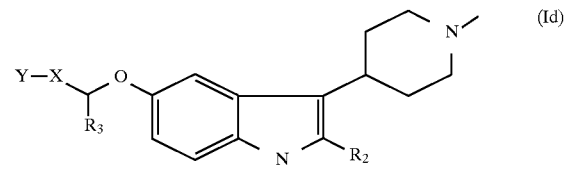
(Id)

a particularly valuable method of preparation consists in condensing an intermediate of general formula (IId)

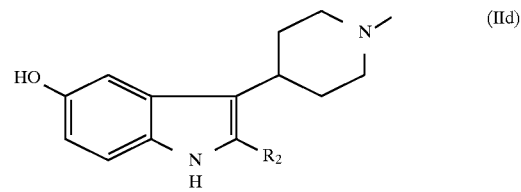
(IId)

with an electrophile of general formula (III) according to the methods and techniques described above. The intermediate of formula (IId) is prepared by condensation of 5-hydroxyindole with a carbonyl-containing derivative of formula (VI)

(VI)

in the presence of sodium methoxide in methanol or of potassium hydroxide in an alcohol followed by the reduction of the double bond by catalytic hydrogenation on $PtO_2$ with hydrogen at atmospheric pressure in methanol.

It will be understood that in certain chemical reactions or series of chemical reactions which lead to the preparation of compounds of general formula (I) it is necessary or desirable to protect sensitive groups or functional groups in the synthesis intermediates in order to avoid undesirable side reactions. This may be carried out using conventional protective groups such as those described in "Protective groups in organic synthesis", T. W. Greene, J. Wiley & Jones, 1981 and "Protecting groups" by P. J. Kocienski, Thieme Verlag, 1994. The suitable protective groups will therefore be introduced and then removed at the level of the most appropriate synthetic intermediates for doing this and using the methods and techniques described in the references cited above.

There should also be considered as forming an integral part of the present invention all the methods which make it possible to convert a derivative of formula (I) to another derivative of formula I by techniques and methods well known to persons skilled in the art. Accordingly, and by way of example, the derivatives of formula (I) in which Y represents a nitrile (CN) may be converted to derivatives of formula (I) in which Y represents $CH_2NH_2$ by a reduction reaction which may be carried out, for example, with the aid of Raney Nickel.

Likewise, a derivative of formula (I) in which Y represents an ester (COOR'$_6$) may also be converted to an amide (Y=CONH$_2$) by reaction with ammonium hydroxide in the presence of ammonium chloride in methanol. The products of formula (I) in which Y represents an ester (CO$_2$R'$_6$) may also be converted to an alcohol by reduction following the methods and techniques which are well known for this type of conversion, such as for example the use of lithium aluminum hydride in a solvent such as ether or THF. The compounds of general formula (I) in which Y represents NH2 are particularly valuable intermediates for the preparation of compounds of formula (I), in which Y represents NHRR"$_6$, NHCOR'$_6$, NHCO$_2$R'$_6$, NHCONHR'$_6$, NHSO$_2$R'$_6$ or NHSO$_2$NR'$_6$R"$_6$, by the methods and techniques which are well known for converting a primary amine to a secondary amine, amide, carbamate, urea, sulfonamide or sulfonurea.

When it is desired to isolate a compound according to the invention in the form of a salt, for example an addition salt with an acid, this may be achieved by treating the free base of general formula (I) with an appropriate acid, preferably in an equivalent quantity, or with creatinine sulfate in an appropriate solvent.

When the processes described above for preparing the compounds of the invention give mixtures of stereoisomers, these isomers may be separated by conventional methods such as preparative chromatography.

When the new compounds of general formula (I) possess one or several asymmetric centers, they may be prepared in the form of a racemic mixture or in the. form of enantiomers either by enantionselective synthesis or by resolution. The compounds of formula (I) possessing at least one asymmetric center may for example be separated into their enantiomers by the usual techniques such as the formation of diastereomeric pairs by formation of a salt with an optically active acid such as (−)-di-p-toluoyl-1-tartaric acid, (+)-di-p-toluoyl-1-tartaric acid, (+)-camphorsulfonic acid, (−)-camphorsulfonic acid, (+)-phenylpropionic acid, (−)-phenylpropionic acid, followed by fractional crystallization and regeneration of the free base. the compounds of formula (I) in which R$_1$ is a hydrogen comprising at least one asymmetric center may also be resolved by formation of diastereomeric amides which are separated by chromatography and hydrolyzed in order to release the chiral auxiliary.

The present invention also relates to the salts, hydrates, solvates and bioprecursors of the compounds exemplified below.

The following examples illustrate the invention without, however, limiting the scope thereof.

EXAMPLE 1

Ethyl 4-[3-(2-aminoethyl)-1H-indol-5-yloxymethyl]benzoate hydrochloride.

1A 3-[2-N-(tert-butoxycarbonyl)aminoethyl]-H-indol-5-ol

The monohydrate creatinesulfate salt of serotonin (102 g, 252 mmol) is treated with di-tert-butyl dicarbonate (82.6 g, 378 mmol) in water (2.1 l) in the presence of 2N sodium hydroxide (420 ml) at room temperature. After 1 hour, the reaction is diluted with ethyl acetate (3 l) and stirred for 10 minutes. The 2 phases formed are separated by decantation; the organic phase is washed with water, dried over sodium sulfate, filtered and then evaporated to dryness. The syrup obtained is chromatographed on a silica gel column, eluted with a dichloromethane/methanol mixture (20:1; v/v). The compound is isolated in the form of a chestnut-colored syrup (65.9 g; 95%).

Elemental analysis (C$_{15}$H$_{20}$N$_2$O$_3$), % calculated: C 65.20; H 7.30; N 10.14; % found: C 64.15; H 7.47; N 9.77. $^1$H NMR, CDCl$_3$ (ppm): 1.44 s, 9H; 2.86 t, 2H; 3.45 m, 2H; 4.68 s, 1H; 5.59 s, 1H; 6.77–7.26 m, 4H; 7.99 s, 1H.

1B Ethyl 4-[3-(2-N-(tert-butoxycarbonyl) aminoethyl]-1H-indol-5-yloxymethyl]benzoate.

A mixture of ethyl 4-(bromomethyl)benzoate (950 mg; 3.9 mmol) of the compound 1A (600 mg; 2.17 mmol) in methyl ethyl ketone (12 ml), in the presence of potassium carbonate (750 mg; 5.4 mmol) and potassium iodide (144 mg; 0.87 mmol) is heated under reflux overnight. The medium is then diluted with dichloromethane, filtered on celite, washed with water and then with a sodium chloride solution. The organic phase is dried over sodium sulfate, filtered and then evaporated to dryness.

The syrup obtained is chromatographed on a silica gel column, eluted with a chloroform/ethyl acetate mixture (15:1; v/v). The pure product is obtained in the form of a colorless syrup (517 mg; 54%).

$^1$H NMR, CDCl$_3$ (ppm): 1.41 t, 3H; 1.50 s, 9H; 2.91 t, 2H; 3.44 t, 2H; 4.41 q, 2H; 5.18 s, 2H; 6.93 dd, 1H; 7.03–8.13 m, 8H.

1 Ethyl 4-[3-(2-aminoethyl)-1H-indol-5-yloxymethyl] benzoate hydrochloride.

The product 1B (370 mg; 0.843 mmol) in solution in toluene (10 ml) is treated with trifluoroacetic acid (1.5 ml). After 3 h at room temperature, the medium is diluted with dichloromethane, washed with 2N sodium hydroxide and then with water. The organic phase is dried over sodium sulfate, filtered and evaporated to dryness. The syrup obtained is chromatographed on a silica gel column, eluted with a dichloromethane/methanol/ammonium hydroxide mixture (90:9.5:0.5; v/v). The pure product is isolated in the form of a colorless syrup which leads, after treatment with hydrochloric acid in ether, to the compound 1 (250 mg; 79%).

Elemental analysis (C$_{20}$H$_{23}$N$_2$O$_3$Cl), % calculated: C 64.08; H 6.18; N 7.47; % found: C 64.04; H 6.21; N 6.91. 1H NMR, DMSO-d6 (ppm): 1.29 t, 3H, 2.98 m, 4H; 4.27 q, 2H; 5.19 S; 2H; 6.80 dd, 1H; 7.18 m, 3H; 7.58 d, 2H; 7.94 m, 5H; 10.82 s, 1H. Melting point: 195°–1960° C.

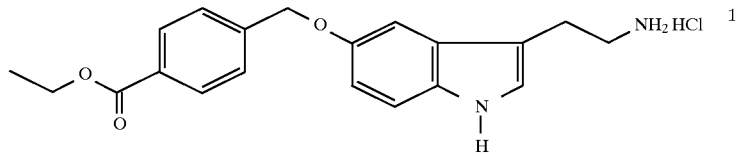

EXAMPLE 2

Methyl 4-[3-(2-aminoethyl)-1H-indol-5-yloxymethyl]benzoate hydrochloride.

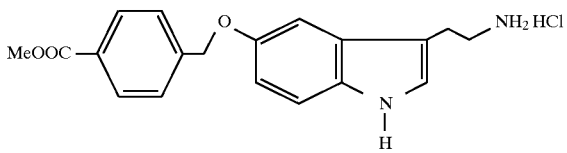

2A Methyl 4-[3-{2-N-(tert-butoxycarbonyl)aminoethyl}-1H-indol -5-yloxymethyl]benzoate.

The product 2A is prepared from methyl 4-(bromomethyl)benzoate (3.25 g; 14.8 mmol) and the compound 1A (2.17 g; 7.88 mmol) according to the procedure described for the preparation of the product 1B.

The syrup obtained is chromatographed on a silica gel column, eluted with a dichloromethane/ethyl acetate mixture (20:1 v/v). The pure product is isolated in the form of a pale yellow syrup which leads, after treatment with hydrochloric acid in ether, to the compound 1 (1.85 g; 55%).

$^1$H NMR, CDC13 (ppm): 1.43 s, 9H; 2.89 t, 2H; 3.40 t, 2H; 3.92 s, 3H; 5.17 s, 2H; 6.94 dd, 1H; 7.00–7.28 m, 3H; 7.53 d, 2H; 8.04 m, 3H.

2 Methyl 4-[3-(2-aminoethyl)-1H-indol-5-yloxymethyl] benzoate hydrochloride.

The product 2 is obtained from the compound 2A (600 mg; 1.41 mmol) according to the method described for the preparation of Example 1 from 1B.

The syrup obtained is chromatographed on a silica gel column, eluted with a dichloromethane/methanol/ammonium hydroxide mixture (90:9.5:0.5 v/v). The pure product is isolated in the form of a beige solid which leads, after treatment with hydrochloric acid in ether, to the compound 2 (367 mg; 71%).

Elemental analysis ($C_{19}H_{21}N_2O_3Cl$), % calculated: C 63.24; H 5.87; N 7.76; % found: C 64.29; H 6.00; N 7.69. $^1$H NMR, DMSO-d6 (ppm): 2.94 m, 4H; 3.86 s, 3H; 5.21 s, 2H; 6.81 dd, 1H; 7.19–8.01 m, 10H; 10.83 s, 1H. Melting point: 230° C. (decomposition).

EAAMPLE 3

{4-[3-(2-Aminoethyl)-1H-indol-5-yloxymethyl]phenyl}methanol hydrochloride.

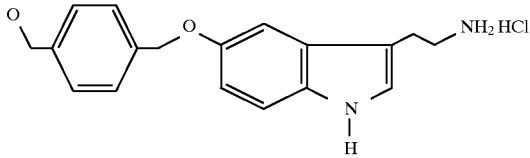

The compound 2A (1.29 g; 3.03 mmol) in solution in anhydrous tetrahydrofuran (30 ml) is treated, at 0° C. and under nitrogen, with lithium aluminum hydride (1M in THF) (3.64 ml; 3.64 mmol). After stirring for 1 h 30 min at room temperature, the medium is treated with a sodium sulfate/water mixture. The precipitate formed is filtered on celite and the solvent is evaporated under reduced pressure. The crude product obtained (1.2 g; 99%) is then deprotected according to the method described for the preparation of Example 1 from 1B.

The syrup obtained is chromatographed on a silica gel column, eluted with a dichloromethane/methanol/ammonium hydroxide mixture (80:18.5:1.5; v/v). The pure product is isolated in the form of a colorless syrup which leads, after treatment with hydrochloric acid in ether, to the compound 3 (466 mg; 46%).

Elemental analysis ($C_{18}H_{21}N_2O_2Cl$. 0.15 $H_2O$), % calculated: C 64.43; H 6.40; H 8.35; % found: C 64.46; H 6.41; N 8.06. $^1$H NMR. DMSO-d6 (ppm): 2.99 s, 4H; 4.99 s, 2H; 5.08 s, 2H; 6.78 dd, 1H; 7.19–7.45 m, 7H; 8.04 s, 3H; 10.83 s, 1H. Melting point: 218° C.

EXAMPLE 4

Propyl 4-[3-(2-aminoethyl)-1H-indol-5-yloxymethyl]benzoate hydrochloride.

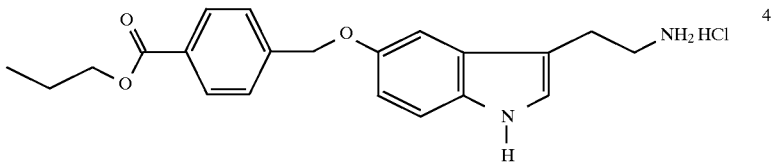

A mixture of propyl 4-(bromomethyl)benzoate (1.6 g; 6.21 mmol) and of the compound 1A (1.1 g; 4.14 mmol) in dimethylformamide (15 ml) in the presence of cesium carbonate (2.16 g; 6.62 mmol) is stirred at room temperature overnight. The medium is then diluted with ethyl acetate, washed with water and,then with a saturated sodium chloride solution. The organic phase is dried over sodium sulfate, filtered and evaporated to dryness.

The syrup obtained is chromatographed on a silica gel column, eluted with a dichloromethane/ethyl acetate mixture (30:1; v/v). The pure product is isolated in the form of a pale yellow syrup (570 mg; 30%). This product is then deprotected according to the conditions described for the preparation of Example 1 from 1B.

The syrup obtained is chromatographed on a silica gel column, eluted with a dichloromethane/methanol/ammonium hydroxide mixture (85:14:1; v/v). The pure product is isolated in the form of a colorless syrup which leads, after treatment with hydrochloric acid in ether, to the compound 4' (401 mg; 82%).

Elemental analysis ($C_{21}H_{25}N_2O_3Cl$), % calculated: C 64.86; H 6.48; N 7.20; Cl 9.12; % found: C 64.56; H 6.42; N 7.17; Cl 9.53. $^1$H NMR DMSO-d6 (ppm): 0.99 t, 3H; 1.67 m, 2H; 2.98 m, 2H; 4.22 t, 2H; 5.21 s, 2H; 6.82 dd, 1H; 7.21 m, 3H; 7.61 d, 2H; 7.96 m, 5H; 10.84 s, 1H. Melting point: 205° C.

EXAMPLE 5

2-[5-(4-Nitrobenzyloxy)-1H-indol-3-yl]ethylamine hydrochloride.

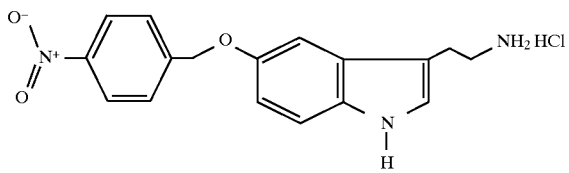

5

The compound 5 is prepared from 4-nitrobenzyl chloride (1 g; 5.8 mmol) and the compound 1A (895 mg, 3.24 mmol) according to the method described for the preparation of Example 1.

The syrup obtained is chromatographed on a silica gel column, eluted with a dichloromethane/methanol/ammonium hydroxide mixture (80:19:1; v/v). The pure product is isolated in the form of orange-yellow crystals which leads, after treatment with hydrochloric acid in ether, to the compound 5 (659 mg, 59%).

Elemental analysis ($C_{17}H_{18}N_3O_3Cl$), % calculated: C 58.71; H 5.22; N 12.08; % found: C 58.91; H 5.18; N 12.01. $^1$H NMR, DMSO-d6 (ppm): 3.00 m, 4H; 5.3 s, 2H; 6.83 dd, 1H; 7.24 m, 3H; 7.80 d, 2H; 8.06 s, 3H; 8.24 d, 2H; 10.87 s, 1H. Melting point: 220° C. (decomposition)

EXAMPLE 6

2-[5-(4-Methyl-3-nitrobenzyloxy)-1H-indol-3-yl]ethylamine hydrochloride.

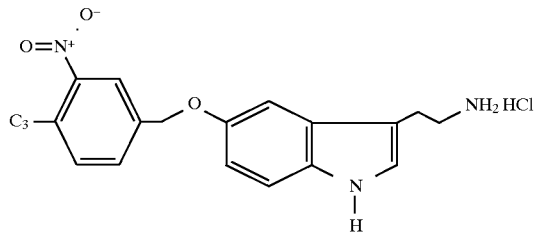

6

The compound 6 is prepared from 4-methyl-3-nitrobenzyl chloride (1 g; 5.38 mmol) and the compound 1A (826 mg; 2.99 mmol) according to the method described for the preparation of Example 1.

The syrup obtained is chromatographed on a silica gel column, eluted with a dichloromethane/methanol/ammonium hydroxide mixture (80:19.5:0.5; v/v). The pure product is isolated in the form of a yellow syrup which leads, after treatment with hydrochloric acid in ether, to the compound 6 (584 mg; 55%).

Elemental analysis ($C_{18}H_{20}N_3O_3Cl$), % calculated: C 59.75; H 5.57; N 11.61; % found: C 60.21; H 5.58; N 11.53. $^1$H NMR, DMSO-d6 (ppm): 2.52 s, 3H; 3.00 m, 4H; 5.20 s, 2H; 6.83 dd, 1H; 7.20 m, 3H; 7.51 d, 1H; 7.72 d, 1H; 7.99 s, 3H; 8.10 d, 1H; 10.86 s, 1H. Melting point: 150° C.

EXAMPLE 7

Methyl 3-[3-(2-aminoethyl)-1H-indol-5-yloxymethyl]benzoate hydrochloride.

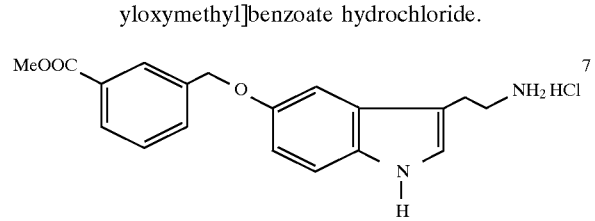

7

The compound 7 is prepared from methyl 3-(bromomethyl)benzoate (745 mg; 3.24 mmol) and the compound 1A (500 mg; 1.80 mmol) according to the method described for the preparation of Example 1.

The syrup obtained is chromatographed on a silica gel column, eluted with a dichloromethane/methanol/ammonium hydroxide mixture (90:9.5:0.5; v/v). The pure product is isolated in the form of a colorless syrup which leads, after treatment with hydrochloric acid in ether, to the compound 7 (383 mg; 59%).

Elemental analysis ($C_{19}H_{21}N_2O_3Cl$), % calculated: C 63.24; H 5.87; N 7.76; % found: C 63.15; H 5.82; N 7.74. $^1$H NMR DMSO-d6 (ppm): 3.01 s, 4H; 3.86 s, 3H; 5.20 s, 3H; 6.82 dd, 1H; 7.20 m, 3H; 7.55 m, 1H; 7.75–8.12 m, 6H; 10.87 d, 1H. Melting point: 185°–186° C.

EXAMPLE 8

2-[5-(2-Nitrobenzyloxy)-1H-indol-3-yl]ethylamine hydrochloride.

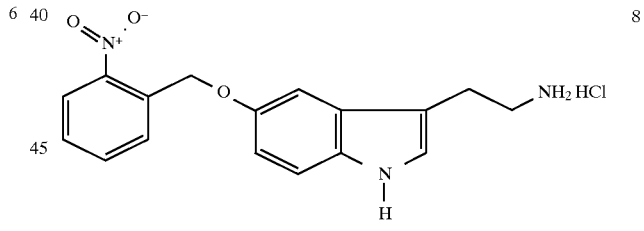

8

The compound 8 is prepared from 2-nitrobenzyl bromide (703 mg; 3.24 mmol) and the compound 1A (600 mg; 2.16 mmol) according to the method described for the preparation of Example 1.

The syrup obtained is chromatographed on a silica gel column, eluted with a dichloromethane/methanol/ammonium hydroxide mixture (90:9.5:0.5; v/v). The pure product is isolated in the form of an orange-colored solid which leads, after treatment with hydrochloric acid in ether, to the compound 8 (439 mg; 58%).

Elemental analysis ($C_{17}H_{18}N_3O_3Cl$), % calculated: C 57.81; H 5.31; N 11.90; % found: C 57.73; H 5.15; N 11.65. $^1$H NMR, DMSO-d6 (ppm): 3.00 s, 4H; 5.44 s, 2H; 6.79 dd, 1H; 7.18–7.30 m, 3H; 7.57–8.11 m, 7H; 10.91 d, 1H. Melting point: 238° C. (decomposition)

EXAMPLE 9

Ethyl 2-[3-(2-aminoethyl)-1H-indol-5-yloxymethyl] benzoate hydrochloride.

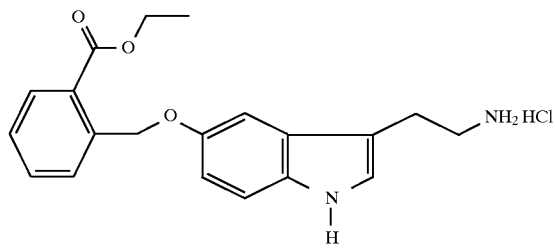

The compound 9 is prepared from ethyl 2-(bromo-methyl) benzoate (4.1 g; 16.84 mmol) and the compound 1A (2.6 g; 9.36 mmol) according to the method described for the preparation of Example 1.

The syrup obtained is chromatographed on a silica gel column, eluted with a dichloromethane/methanol/ ammonium hydroxide mixture (90:9.5:0.5; v/v). The pure product is isolated in the form of a colorless syrup which leads, after treatment with hydrochloric acid in ether, to the compound 9 (1.84 g; 52%).

Elemental analysis ($C_{20}H_{23}N_2O_3Cl$), % calculated: C 64.08; H 6.18; N 7.47; % found: C 63.82; H 6.25; N 7.22. $^1$H NMR. DMSO-d6 (ppm): 1.20 t, 3H; 2.97 s, 4H; 4.20 q, 2H; 5.38 s, 2H; 6.74 dd, 1H; 7.12–8.04 m, 10H; 10.86 s, 1H.

Melting point: 235° C. (decomposition)

EXAMPLE 10

2-[3-(2-Aminoethyl)-1H-indol-5-yloxymethyl]-1-phenylethanone hydrochloride

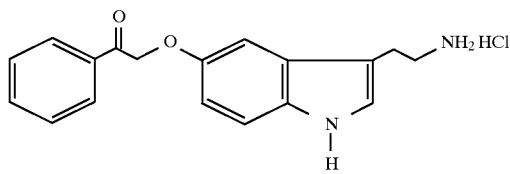

The compound 10 is prepared from 2-chloro-1-phenylethanone (1 g; 6.46 mmol) and the compound 1A (993 mg; 3.59 mmol) according to the method described for the preparation of Example 1.

The syrup obtained is chromatographed on a silica gel column, eluted with a dichloromethane/methanol/ ammonium hydroxide mixture (80:19:1; v/v). The pure product is isolated in the form of a yellow syrup which leads, after treatment with hydrochloric acid in ether, to the compound 10 (254 mg; 22%).

Elemental analysis ($C_{18}H_{19}N_2O_2Cl$), % found: C 65.35; H 5.79; N 8.47; % found: C 64.41; H 5.75; N 8.60 $^1$H NMR, DMSO-d6 (ppm): 2.98 m, 4H; 5.52 s, 2H; 6.80 dd, 1H; 7.20 m, 3H; 7.52–7.68 m, 3H; 8.05 m, 5H; 10.87 s, 1H.

Melting point: 131° C.

EXAMPLE 11

2-[3-(2-Aminoethyl)-1H-indol-5-yloxy]-1-(4-methoxyphenyl)ethanone hydrochloride.

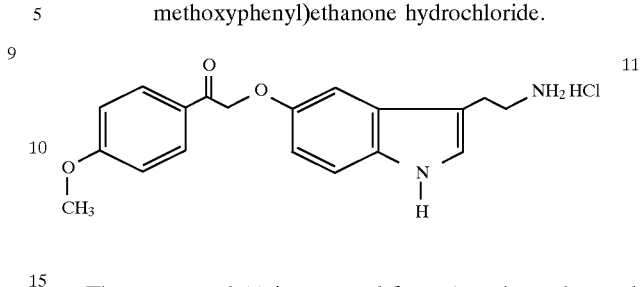

The compound 11 is prepared from 4-methoxyphenacyl bromide (622 mg; 2.7 mmol) and the compound 1A (500 mg; 1.81 mmol) according to the method described for the preparation of Example 4.

The syrup obtained is chromatographed on a silica gel column, eluted with a dichloromethane/methanol/ ammonium hydroxide mixture (80:18.5:1.5; v/v). The pure product is isolated in the form of a yellow syrup which leads, after treatment with hydrochloric acid in ether, to the compound 11 (256 mg; 40%).

Elemental analysis ($C_{19}H_{21}N_2O_3Cl.H_2O$), % calculated: C 60.24; H 6.12; N 7.39; Cl 9.36; % found: C 60.29; H 5.95; N 7.28; Cl 9.29. $^1$H NMR, DMSO-d6 (ppm): 3.01 m, 4H; 3.85 s, 3H; 5.42 s, 2H; 6.78 dd, 1H; 7.05–7.27 m, 5H; 7.93–8.05 m, 5H; 10.83 s, 1H. Melting point: 144° C.

EXAMPLE 12

Ethyl 4-[3-(2-aminoethyl)-1H-indol-5-yloxy)-butyrate hydrochloride

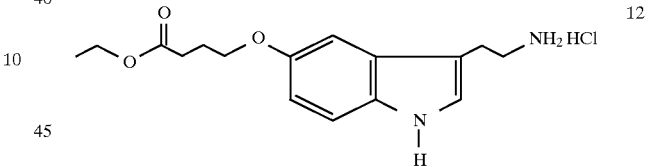

The compound 12 is prepared from ethyl 4-bromo-butyrate (1.87 ml; 13.03 mmol) and the compound 1A (2 g; 7.24 mmol) according to the method described for the preparation of Example 1.

The syrup obtained is chromatographed on a silica gel column, eluted with a dichloromethane/methanol/ ammonium hydroxide mixture (80:18.5:1.5; v/v). The pure product is isolated in the form of a colorless syrup which leads, after treatment with hydrochloric acid in ether, to the compound 12 (1.14 g; 48%).

Elemental analysis ($C_{16}H_{23}N_2O_3Cl$), % calculated: C 58.80; H 7.09; N 8.57; % found: C 58.92; H 6.93; N 8.58. $^1$H NMR, DMSO-d6 (ppm): 1.18 t, 3H; 1.94 m, 2H; 2.50 t, 2H; 2.99 s, 4H; 4.01 m, 4H;, 6.71 dd, 1H; 7.06–7.26 m, 3H; 8.07 S, 1H; 10.82 s, 1H. Melting point: 173° C. (decomposition)

EXAMPLE 13

Ethyl 5-[3-(2-aminoethyl)-1H-indol-5-yloxy]pentanoate hydrochloride.

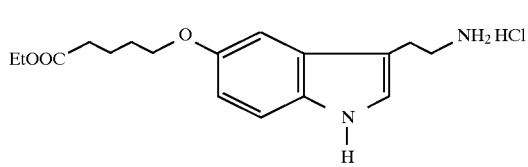

13

The compound 13 is prepared from ethyl 5-bromovalerate (3.1 ml; 19.54 mmol) and the compound 1A (3 g; 10.86 mmol) according to the method described for the preparation of Example 1.

The syrup obtained is chromatographed on a silica gel column, eluted with a dichloromethane/methanol/ammonium hydroxide mixture (80:19:1; v/v). The pure product is isolated in the form of a beige syrup which leads, after treatment with hydrochloric acid in ether, to the compound 13 (1.87 g; 51%).

Elemental analysis ($C_{17}H_{25}N_2O_3Cl$), % calculated: C 59.91; H 7.39; N 8.22; % found: C 59.51; H 7.27; N 8.01.

$^1$H NMR, DMSO-d6 (ppm): 1.16 t, 3H; 1.69 m, 4H;, 2.32 t, 2H; 2.97 m, 4H; 3.98 m, 4H; 6.69 dd, 1H; 7.05–7.24 m, 3H; 8.05 s, 3H; 10.81 s, 1H. Melting point: 177° C.

EXAMPLE 14

Ethyl 6-[3-(2-aminoethyl)-1H-indol-5-yloxy]hexanoate hydrochloride.

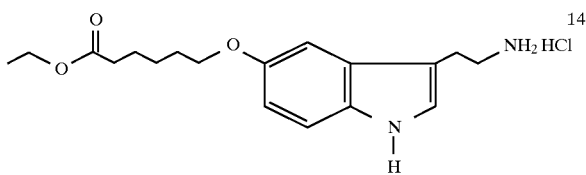

14

The compound 14 is prepared from ethyl 6-bromohexanoate (1.3 ml, 7.24 mmol) and the compound 1A (1 g; 3.62 mmol) according to the method described for the preparation of Example 1.

The syrup obtained is chromatographed on a silica gel column, eluted with a -dichloromethane/methanol/ammonium hydroxide mixture (80:19:1; v/v). The pure product is isolated in the form of a pale yellow syrup which leads, after treatment with hydrochloric acid in ether, to the compound 14 (746 mg; 58%).

Elemental analysis ($C_{18}H_{27}N_2O_3Cl$), % calculated: C 60.92; H 7.67; N 7.89; Cl 9.99; % found: C 60.72; H 7.64; N 7.80; Cl 10.03. $^1$H NMR, DMSO-d6 (ppm): 1.16 t, 3H; 1.38–1.78 m, 6H; 2.30 t, 2H; 2.98 s, 4H; 3.91–4.09 m, 4H; 6.69 dd, 1H; 7.05–7.24 m, 3H; 8.10 s, 3H; 10.81 s, 1H. Melting point: 170° C.

EXAMPLE 15

Benzyl 6-[3-(2-aminoethyl)-1H-indol-5-yloxy]hexanoate hydrochloride.

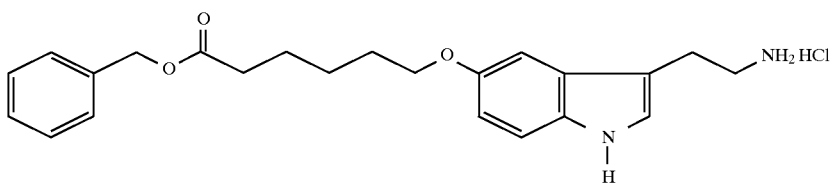

15

The compound 15 is prepared from benzyl 6-bromohexanoate (929 mg; 3.25 mmol) and the compound 1A (500 mg; 1.81 mmol) according to the method described for the preparation of Example 1.

The syrup obtained is chromatographed on a silica gel column, eluted with a dichloromethane/methanol/ammonium hydroxide mixture (85:14:1; v/v). The pure product is isolated in the form of a yellow syrup which leads, after treatment with hydrochloric acid in ether, to the compound 15 (479 mg; 64%).

Elemental analysis ($C_{23}H_{29}N_2O_3Cl$), % calculated: C 66.26; H 7.01; N 6.72; Cl 8.50; % found: C 66.05; H 6.95; N 6.65; Cl 8.40. $^1$H NMR DMSO-d6 (ppm): 1.44–1.76 m, 6H; 2.40 t, 2H; 2.99 s, 4H; 3.95 t, 2H; 5.09 s, 2H; 6.70 dd, 1H; 7.06–7.36 m, 8H; 8.05 s, 3H; 10.82 s, 1H. Melting point: 130° C.

EXAMPLE 16

Isopropyl 6-[3-(2-aminoethyl)-1H-indol-5-yloxy]hexanoate hydrochloride.

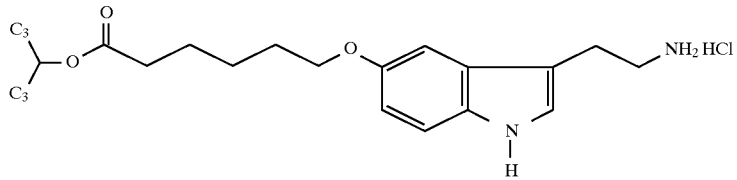

16

The compound 16 is prepared from isopropyl 6-bromohexanoate (772 mg; 3.25 mmol) and the compound 1A (500 mg; 1.81 mmol) according to the method described for the preparation of Example 1.

The syrup obtained is chromatographed on a silica gel column, eluted with a dichloromethane/methanol/ammonium hydroxide mixture (80:19:1; v/v). The pure product is isolated in the form of a colorless syrup which leads, after treatment with hydrochloric acid in ether, to the compound 16 (369 mg; 55%).

Elemental analysis ($C_{19}H_{29}N_2O_3Cl$), % calculated: C 61.86; H 7.92; N 7.59; Cl 9.61; % found: C 61.91; H 7.93; N 7.49; Cl 9.64. $^1$H NMR, DMSO-d6 (ppm): 1.26 d, 6H; 1.43–1.76 m, 6H; 2.28 t, 2H; 2.98 m, 4H; 3.95 t, 2H; 4.88 m, 1H; 6.70 dd, 1H; 7.05–7.26 m, 3H; 8.01 s, 3H; 10.80 s, 1H. Melting point: 137° C.

EXAMPLE 17

6-[3-(2-Aminoethyl)-1H-indol-5-yloxy]hexa-nitrile hydrochloride

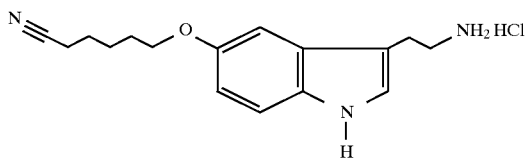

17A 6-[3-(2-N-(tert-Butoxycarbonyl)aminoethyl)-1H-indol-5-yloxy]hexanitrile

The compound 17A is prepared from 6-bromocapronitrile (2.87 g, 16.29 mmol) and the compound 1A (2.5 g; 9.04 mmol) according to the method described for the preparation of Example 1B.

The syrup obtained is chromatographed on a silica gel column, eluted with a dichloromethane/acetone mixture (20:1; v/v). The pure product is isolated in the form of a yellow syrup (3.17 g; 94%).

17 6-[3-(2-Aminoethyl)-1H-indol-5-yloxy]hexanitrile hydrochloride

The compound 17A (650 mg, 1.75 mmol) is then deprotected according to the method described for the preparation of Example 1 from 1B.

The syrup obtained is chromatographed on a silica gel column, eluted with a dichloromethane/methanol/ammonium hydroxide mixture (80:19:1; v/v). The pure product is isolated in the form of a pale yellow syrup which leads, after treatment with hydrochloric acid in ether, to the compound 17 (436 mg; 81%).

Elemental analysis ($C_{16}H_{22}N_3OCl$, 0.5 $H_2O$), % calculated: C 60.65; H 7.32; N 13.29; Cl 11.18; % found: C 60.67; H 7.03; N 12.92; Cl 11.54. $^1$H NMR, DMSO-d6 (ppm): 1.56–1.73 m, 6H; 2.48 t, 2H; 2.96 s, 4H; 3.95 t, 2H; 6.70 dd, 1H; 7.05–7.24 m, 3H; 8.02 s, 3H; 10.80 s, 1H. Melting point: 124° C.

EXAMPLE 18

6-[3-(2-Aminoethyl)-1H-indol-5-yloxy]hexylamine hydrochloride.

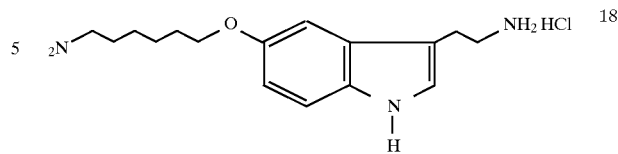

18A 6-{3-[2-N-(tert-Butoxycarbonyl)aminoethyl]-1H-indol-5-yloxy}hexylamine.

The compound 17A.(2.49 g; 6.69 mmol) in solution in tetrahydrofuran (93 ml), in the presence of ammonium hydroxide (6.2 ml) and Raney Nickel (2 spatulas), is subjected to an atmospheric hydrogen pressure for 25 hours. The mixture is then filtered on celite and the solvent evaporated to dryness.

The syrup obtained is chromatographed on a silica gel column, eluted with a dichloromethane/methanol/ammonium hydroxide mixture (80:19:1; v/v). The pure product is isolated in the form of a colorless syrup (2.45 g; 97%).

$^1$H NMR. DMSO-d6 (ppm): 1.37 m, 15H; 1.68 m, 2H; 2.49 m, 2H; 2.73 t, 2H; 3.14 m, 2H; 3.93 t, 2H; 6.67 dd, 1H; 6.87–7.24 m, 4H; 10.61 s, 1H.

18 6-[3-(2-Aminoethyl)-1H-indol-5-yloxy]hexylamine hydrochloride.

The product 18A (800 mg; 2.13 mmol) is then deprotected according to the method described for the preparation of Example 1 from 1B.

The syrup obtained is chromatographed on a silica gel column, eluted with a dichloromethane/methanol/ammonium hydroxide mixture (75:20:5; v/v). The pure product is isolated in the form of a colorless syrup which leads, after treatment with hydrochloric acid in ether, to the compound 18 (556 mg; 75%).

Elemental analysis ($C_{16}H_{27}N_3OCl_2$, $H_2O$), a calculated: C 52.46; H 7.98; N 11.47; Cl 19.36; % found: C 52.41; H 7.46; N 11.05; Cl 21.75. $^1$H NMR, DMSO-d6 (ppm): 1.45–1.74 m, 8H; 2.76 m, 2H; 3.00 s, 4H; 3.99 t, 2H; 6.72 dd, 1H; 7.10–7.27 m, 3H; 8.17 m, 6H; 10.84 s, 1H. Melting point: 100° C.

EXAMPLE 19

N-{6-[3-(2-Aminoethyl)-1H-indol-5-yloxy]hexyl}methanesulfonamide hydrochloride

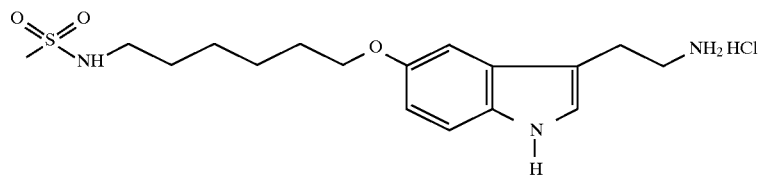

The product 18A (900 mg; 2.39 mmol) in solution in dichloromethane (25 ml) in the presence of triethylamine (500 μl; 3.59 mmol) is treated, at room temperature and under nitrogen, with mesyl chloride (223 μl; 2.87 mmol). After stirring for one hour, the medium is diluted with dichloromethane and washed with water. The organic phase is dried over sodium sulfate, filtered and evaporated to dryness.

The crude product obtained is taken up in dichloromethane (15 ml) and treated with a solution of hydrochloric acid in ether in the presence of a few drops of water for 12 hours. This method makes it possible to obtain directly the compound 19 in the form of pale green crystals (743 mg; 80%).

Elemental analysis (C$_{17}$H$_{28}$N$_3$O$_3$SCl), % calculated: C 52.36; H 7.24; N 10.78; Cl 9.09; % found: C 52.07; H 7.20; N 10.60; Cl 9.69. $^1$H NMR, DMSO-d6 (ppm): 1.41–1.73 m, 8H; 2.88–2.99 m, 9H; 3.97 t, 2H; 6.72 dd, 1H; 6.97–7.26 m, 4H; 8.07 s, 3H; 10.82 s, 1H. Melting point: 160° C.

EXAMPLE 20

6-[3-(2-Aminoethyl)-1H-indol-5-yloxy]-N-ethylhexanamide hydrochloride

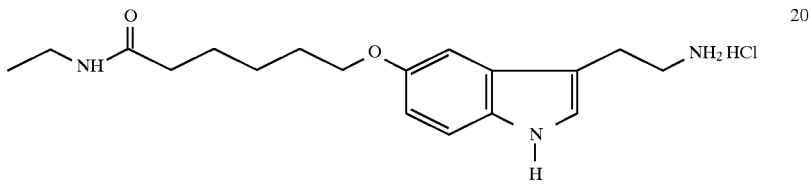

The compound 20 is prepared from 6-bromo-N-ethylhexanamide (362 mg; 1.63 mmol) and the compound 1A (300 mg; 1.09 mmol) according to the method described for the preparation of Example 4.

The product obtained is deprotected under the conditions described for the preparation of Example 19. The compound 20 is thus obtained in the form of a white powder (217 mg; 56%).

Elemental analysis (C$_{18}$H$_{21}$N$_3$O$_2$Cl, 0.5 H$_2$O), % calculated: C 59.58; H 8.05; N 11.58; Cl 9.77; % found: C 59.52, H 7.84; N 11.32; Cl 11.13 $^1$H NMR, DMSO-d6 (ppm): 0.96 t, 3H; 1.37–1.72 m, 6H; 2.05 t, 2H; 2.98 m, 6H; 3.92 t, 2H; 6.67 dd, 1H; 7.03–7.23 m, 3H; 7.81 s, 1H; 8.05 s, 3H; 10.79 s, 1H. Melting point: 195° C.

EXAMPLE 21

Isopropyl 5-[3-(2-aminoethyl)-1H-indol-5-yloxy]pentanoate hydrochloride

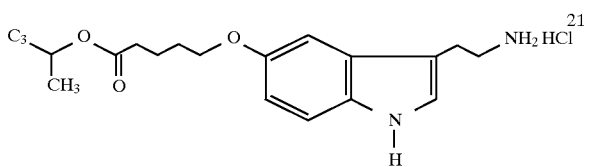

The compound 21 is prepared from isopropyl 5-bromopentanoate (727 mg; 3.26 mmol) and the compound 1A (500 mg; 1.81 mmol) according to the method described for the preparation of Example 1.

The syrup obtained is chromatographed on a silica gel column, eluted with a dichloromethane/methanol/ammonium hydroxide mixture (85:14:1; v/v). The pure product is isolated in the form of a yellow syrup which leads, after treatment with hydrochloric acid in ether, to the compound 21 (159 mg; 25%).

Elemental analysis (C$_{18}$H$_{27}$N$_2$O$_3$Cl), % calculated: C 60.94; H 7.67; N 7.89; Cl 9.99; % found: C 61.06; H 7.80; N 7.57; Cl 9.50. $^1$H NMR DMSO-d6 (ppm): 1.16 d, 6H; 1.71 m, 4H; 2.33 t, 2H; 2.98 m, 4H; 3.96 t, 2H; 4.89 m, 1H; 6.71 dd, 1H; 7.05–7.26 m, 3H; 7.96 s, 3H; 10.80 s, 1H. Melting point: 130° C.

EXAMPLE 22

Benzyl 5-[3-(2-aminoethyl)-1H-indol-5-yloxy]pentanoate hydrochloride

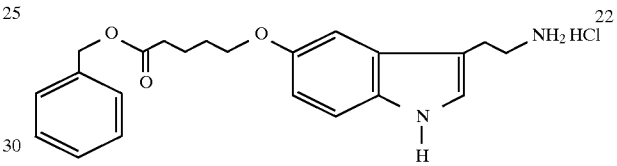

The compound 22 is prepared from benzyl 5-bromopentanoate (883 mg; 3.25 mmol) and the compound 1A (500 mg; 1.81 mmol) according to the method described for the preparation of Example 1.

The syrup obtained is chromatographed on a silica gel column, eluted with a dichloromethane/methanol/ammonium hydroxide mixture (85:14:1; v/v). The pure product is isolated in the form of a colorless syrup which leads, after treatment with hydrochloric acid in ether, to the compound 22 (449 mg; 62%).

Elemental analysis (C$_{22}$H$_{27}$N$_2$O$_3$Cl), a calculated: C 65.58, H 6.75; N 6.95; Cl 8.79; % found: C 65.15; H 6.77; N 6.90; Cl 8.92 $^1$H NMR, DMSO-d6 (ppm): 1.72 m, 4H; 2.44 m, 2H; 2.99 m, 4H; 3.96 m, 2H; 6.69 dd, 1H; 7.06–7.34 m, 8H; 8.08 s, 3H; 10.83 s, 1H. Melting point: 162° C.

EXAMPLE 23

4-[3-(2-Aminoethyl)-1H-indol-5-yloxy]butylacetate hydrochloride

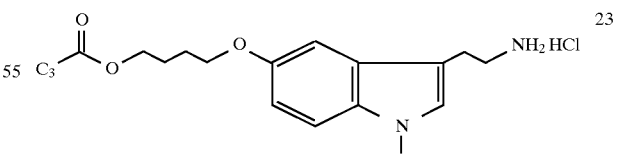

23A 4-[3-(2-N-tert-Butoxycarbonyl)aminoethyl)-1H-indol-5-yloxy]butylacetate

The compound 23A is obtained from butyl 4-bromoacetate (0.94 ml; 6.5 mmol) and the compound 1A (1 g; 3.62 mmol) according to the method described for the preparation of the product 1B.

The syrup obtained is purified on a silica gel column, eluted with a dichloromethane/acetone mixture (20:1, v/v).

The pure product is isolated in the form of a pale yellow syrup (1.26 g; 89%).

23  4-[3-(2-Aminoethyl)-1H-indol-5-yloxy]butylacetate hydrochloride

The compound 23A (508 mg; 1.30 mmol) is then deprotected according to the method described for the preparation of Example 1 from 1B.

The syrup obtained is chromatographed on a silica gel column, eluted with a dichloromethane/methanol/ammonium hydroxide mixture (80:18.5:1.5; v/v). The pure product is isolated in the form of a colorless syrup which leads, after treatment with hydrochloric acid in ether, to the compound 23 (309 mg.; 73%).

Elemental analysis ($C_{16}H_{23}N_2O_3Cl$), % calculated: C 58.81; H 7.09; N 8.57; Cl 10.85; % found: C 58.71; H 7.11, N 8.41; Cl 10.59 $^1$H NMR, DMSO-d6 (ppm): 1.76 m, 4H; 2.01 s, 3H; 2.98 m, 4H; 3.99–4.08 m, 4H; 6.72 dd, 1H; 7.07–7.27 m, 3H; 7.99 s, 3H; 10.81 s, 1H; Melting point: 171° C.

EXAMPLE 24

4-[3-(2-Aminoethyl)-1H-indol-5-yloxy]butan-1-ol hydrochloride

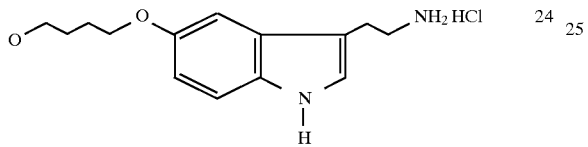

The compound 23A (706 mg; 1.81 mmol) in solution in ethanol (12.5 ml) is treated with potassium hydroxide (203 mg; 3.62 mmol), at room temperature for 4 h 30 min. The medium is then diluted with water and the pH is adjusted to 2–3 by addition of a normal hydrochloric acid solution. This mixture is then extracted with ethyl acetate; the organic phase is dried over sodium sulfate, filtered and evaporated to dryness. The crude product obtained is then deprotected according to the method described for the preparation of Example 1 from 1B.

The syrup obtained is chromatographed on a silica gel column, eluted with a dichloromethane/methanol/ammonium hydroxide mixture (85:14:1; v/v). The pure product is isolated in the form of a pale yellow syrup which leads, after treatment with hydrochloric acid in ether, to the compound 24 (252 mg; 50%).

Elemental analysis ($C_{14}H_{21}N_2O_2Cl$, 0.2 $H_2O$) % calculated: C 58.31; H 7.48; N 9.71 Cl 12.29; % found: C 58.15; H 7.19; N 9.49; Cl 12.26. $^1$H NMR, DMSO-d6 (ppm): 1.59–1.77 m, 4H; 3.00 m, 4H; 3.49 m, 2H; 3.99 t, 2H; 4.49 t, 1H; 6.73 d, 1H; 7.06–7.28 m, 3H; 7.93 s, 3H; 10.81 s, 1H. Melting point: 184° C.

EXAMPLE 25

5-[3-(2-Aminoethyl)-1H-indol-5-yloxyl]-N-ethylpentanamide hydrochloride.

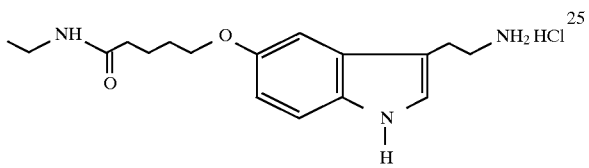

The compound 25 is prepared from 5-bromo-N-ethylpentanamide (339 mg; 1.62 mmol) and the compound 1A (300 mg; 1.09 mmol) according to the method described for the preparation of Example 4.

The syrup obtained is chromatographed on a silica gel column, eluted with a dichloromethane/methanol/ammonium hydroxide mixture (80:18:2; v/v). The pure product is isolated in the form of a pale yellow syrup which leads, after treatment with hydrochloric acid in ether, to the compound 25 (179 mg; 48%).

Elemental analysis ($C_{17}H_{26}N_3O_2Cl$, 0.4 $H_2O$), % calculated: C 58.83, H 7.78; N 12.11, Cl 10.21; % found: C 58.84; H 7.56; N 11.81; Cl 11.07 $^1$H NMR. DMSO-d6 (ppm): 0.97 t, 3H; 1.65 m, 4H; 2.09 t, 2H; 2.96 m, 6H; 3.93 m, 2H; 6.68 dd, 1H; 7.04–7.23 m, 3H; 7.84 s, 1H; 8.03 s, 3H; 10.78 s, 1H Melting point: 184° C.

EXAMPLE 26

5-[3-(2-Aminoethyl)-1H-indol-5-yloxy]pentanenitrile hydrochloride

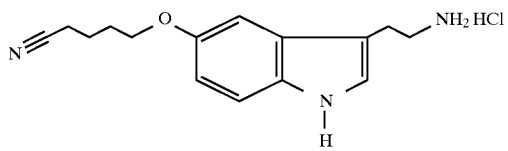

26A  5-{3-[2-N-(tert-Butoxycarbonyl)aminoethyl]-1H-indol-5-yloxy}pentanenitrile.

The compound 26A is prepared from 5-bromovaleronitrile (1.9 ml; 16.29 mmol) and the compound 1A accord to the procedure described for the preparation of the product 1B.

The syrup obtained is chromatographed on a silica gel column, eluted with a dichloromethane/acetone mixture (40:1; v/v). The pure product is isolated in the form of 5 a pale yellow syrup (2.94 g; 91%).

$^1$H NMR, DMSO-d6 (ppm): 1.35 s, 9H; 1.74 m, 4H; 2.56 t, 2H; 2.72 t, 2H; 3.14 m, 2H; 3.97 t, 2H; 6.68 dd, 1H; 6.82–7.32 m, 4H; 10.60 s, 1H.

26  5-[3-(2-Aminoethyl]-1H-indol-5-yloxy]pentanenitrile hydrochloride.

The compound 26A (600 mg; 1.67 mmol) is then deprotected according to the method described for the preparation of the Example 1 from 1B.

The syrup obtained is chromatographed on a silica gel column, eluted with a dichloromethane/methanol/ammonium hydroxide mixture (85:14:1; v/v). The pure product is isolated in the form of a colorless syrup which leads, after treatment with hydrochloric acid in ether, to the compound 26 (304 mg; 62%).

Elemental analysis ($C_{15}H_{20}N_3O_1Cl$), % calculated: C 61.32;

H 6.86; N 14.30; Cl 12.07; % found: C 60.87; H 6.77; N 13.96; Cl 11.37 $^1$H NMR, DMSO-d6 (ppm): 1.78 m, 4H; 2.61 t, 2H; 3.01 m, 4H; 4.02 t, 2H; 6.74 dd, 1H; 7.10–7.28 m, 3H; 8.06 s, 3H; 10.83 s, 1H. Melting point: 182° C.

EXAMPLE 27

5-[3-(2-Aminoethyl)-1H-indol-5-yloxy]pentylamine hydrochloride

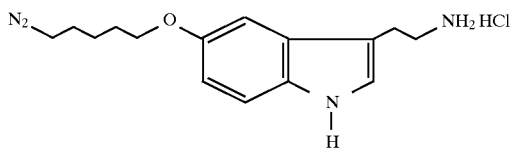

27A 5-{3-[2-N-(tert-Butoxycarbonyl)aminoethyl]-1H-indol-5-yloxy}pentylamine

The compound 26A (2.34 g; 6.55 mmol) in solution in tetrahydrofuran (88 ml), in the presence of ammonium hydroxide (5.9 ml) and Raney Nickel (2 spatulas), is subjected to an atmospheric hydrogen pressure for 26 hours.

The mixture is then filtered on celite and the solvent evaporated to dryness. The syrup obtained is purified on a silica gel column, eluted with a dichloromethane/methanol/ammonium hydroxide mixture (80:18.5:1.5; v/v).

The pure product is obtained in the form of a colorless syrup (1.27 g; 54%).

$^1$H NMR, DMSO-d6 (ppm): 1.40–1.70 m, 15H; 2.56–3.25 m, 6H; 3.97 t, 2H; 6.70 dd, 1H; 7.01–7.28 m, 4H; 10.58 s, 1H.

27 5-[3-(2-Aminoethyl)-1H-indol-5-yloxy]pentylamine hydrochloride

The product 27A (522 mg; 1.44 mmol) is deprotected according to the method described for the preparation of Example 1 from 1B.

The syrup obtained is chromatographed on a silica gel column, eluted with a dichloromethane/methanol/ammonium hydroxide mixture (75:20:5; v/v). The pure product is isolated in the form of white crystals which lead, after treatment with hydrochloric acid in ether, to the compound 27 (307 mg; 62%).

Elemental analysis ($C_{15}H_{25}N_3O_1Cl_2$), % calculated: C 52.21; H 7.65; N 12.18; Cl 20.55; % found: C 52.07; H 7.30; N 11.83; Cl 19.27 $^1$H NMR, DMSO-d6 (-pm): 1.48–1.73 m, 6H; 2.78 t, 2H; 2.98 m, 4H; 3.97 t, 2H; 6.71 dd, 1H; 7.09–7.26 m, 3H; 7.81 broad s, 6H; 10.83 s, 1H. Melting point: 123° C.

EXAMPLE 28

N-{5-[3-(2-Aminoethyl)-1H-indol-5-yloxy]pentyl}methanesulfonamide hydrochloride

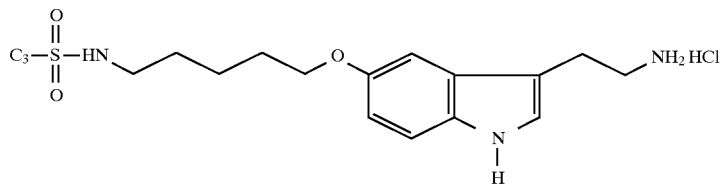

The product 28 is prepared from the compound 27A (559 mg; 1.54 mmol) according to the method described for the preparation of Example 19.

The crude product is then deprotected according to the method described for the preparation of Example 1 from 1B.

The syrup obtained is chromatographed on a silica gel column, eluted with a dichloromethane/methanol/ammonium hydroxide mixture (80:18.5:1.5; v/v). The pure product is isolated in the form of a pale yellow syrup which leads, after treatment with hydrochloric acid in ether, to the compound 28 (396 mg; 68%).

Elemental analysis ($C_{16}H_{26}N_3O_3S_1Cl$), % calculated: C 51.12; H 6.97; N 11.18; Cl 9.43; % found: C 51.23; H 6.97; N 10.78; Cl 9.69 $^1$H NMR, DMSO-d6 (ppm): 1.52 m, 4H; 1.71 m, 2H; 2.88–2.99 m, 9H; 3.97 t, 2H; 6.72 dd, 1H; 6.98–7.27 m, 4H; 8.02 s, 3H; 10.81 s, 1H. Melting point: 147° C.

EXAMPLE 29

Methyl (±)-[3-(2-aminoethyl)-1H-indol-5-yloxy]phenylacetate hydrochloride

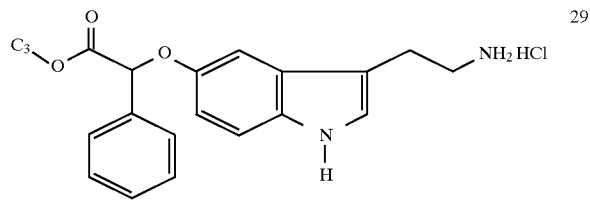

29A Methyl (±)-{3-[2-N-(tert-butoxycarbonyl) aminoethyl]-1H-indol-5-yloxy}phenylacetate The compound 29A is obtained from methyl (±)-α-bromophen-ylacetate (5.1 ml; 32.56 mmol) and the compound 1A (5 g; 18.09 mmol) according to the method described for the preparation of the product 1B.

The syrup obtained is chromatographed on a silica gel column, eluted with a hexane/ethyl acetate mixture (2:1 then 1:1; v/v). The pure product is isolated in the form of a pink foam (5.95 g; 77%).

$^1$H NMR, CDCl$_3$ (ppm): 1.45 s, 9H; 2.87 t, 2H; 3.40 m, 2H; 3.75 s, 3H; 5.70 s, 1H; 6.85–7.66 m, 9H; 8.14 s, 1H.

29 Methyl (±)-[3-(2-aminoethyl)-1H-indol-5-yloxy]phenylacetate hydrochloride

The compound 29A (500 mg; 1.18 mmol) is deprotected according to the method described for the preparation of Example 1 from 1B.

The syrup obtained is chromatographed on a silica gel column, eluted with a dichloromethane/methanol/ammonium hydroxide mixture (80:19.5:0.5; v/v). The pure product is isolated in the form of a colorless syrup which leads, after treatment with hydrochloric acid in ether, to the compound 29 (237 mg; 60%).

Elemental analysis ($C_{19}H_{21}N_2O_3Cl$), % calculated: C 63.24; H 5.87; N 7.76; % found: C 63.21; H 5.81; N 7.78 $^1$H NMR, DMSO-d6 (ppm): 2.98 m, 4H; 3.65 s, 3H; 5.98 s, 1H; 6.82 dd, 1H; 7.11–7.62 m, 8H; 8.08 s, 3H; 10.89 s, 1H. Melting point: 193° C. (decomposition)

EXAMPLE 30

(±)-2-[3-(2-aminoethyl)-1H-indol-5-yloxy]-2-phenylethanol hydrochloride.

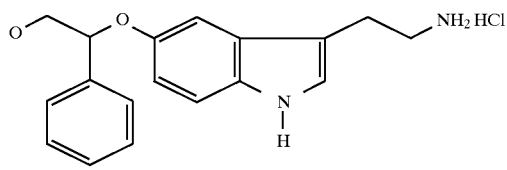

The compound 29A (400 mg; 0.96 mmol) in solution in anhydrous tetrahydrofuran (10 ml) is treated, under nitrogen and at 0° C., with lithium aluminum hydride (72 mg; 1.92 mmol). The medium is stirred at room temperature for 3 hours. The mixture is then treated with a sodium sulfate/water mixture in order to hydrolyze the excess reagent. The paste formed is filtered on celite and then it is washed with tetrahydrofuran and with ethyl acetate. The solvents are evaporated under reduced pressure to give a brown syrup. This syrup is purified on a silica gel column, eluted with a dichloromethane/acetone mixture (15:1; v/v). The pure product is isolated in the form of a brown syrup (398 mg; 84%).

This syrup is then taken up in dichloromethane (5 ml) and treated with a solution of hydrochloric acid in ether in the presence of a few drops of water. After 1 hour, the white crystals formed are isolated to give the compound 30 (150 mg; 46%).

Elemental analysis ($C_{18}H_{21}N_2O_2Cl$, 0.4 $H_2O$), % calculated: C 63.58; H 6.46; N 8.24; % found: C 63.81; H 6.20; N 8.03 $^1$H NMR, DMSO-d6 (ppm): 2.94 m, 4H; 3.57–3.83 m, 2H; 5.10 m, 1H; 6.74 dd, 1H; 7.04–7.46 m, 8H; 7.95 s, 3H; 10.76 s, 1H. Melting point: 200° C.

EXAMPLE 31

(±)-[3-(2-Aminoethyl)-1H-indol-5-yloxy]phenylacetic acid hydrochloride

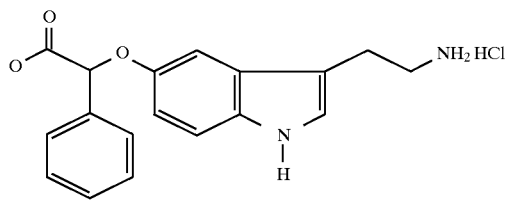

31A (±)-{3-[2-(tert-Butoxycarbonyl)aminoethyl]-1H-indol-5-yloxy}phenylacetic acid The compound 29A (600 mg; 1.41 mmol) in solution in ethanol (6 ml) is treated with potassium hydroxide (316 mg; 5.6 mmol) at room temperature for 1 h 30 min.

The medium is then diluted with ethyl acetate and washed with a normal hydrochloric acid solution to pH 3. The organic phase is dried over sodium sulfate, filtered and evaporated to dryness.

The syrup obtained is chromatographed on a silica gel column, eluted with a dichloromethane/methanol mixture (5:1; v/v). The pure product is isolated in the form of a syrup giving a beige foam upon evaporation (578 mg; 99%).

Elemental analysis ($C_{23}H_{26}N_2O_5$, 0.5 $H_2O$), % calculated: C 65.86; H 6.49; N 6.68; % found: C 66.00; H 6.61; N 6.23 $^1$H NMR, CDCl$_3$ (ppm): 1.42 s, 9H; 2.81 t, 2H; 3.35 m, 2H; 5.68 s, 1H; 6.90–7.67 m, 9H; 8.03 s, 1H 31 (±)-[3-(2-Aminoethyl)-1H-indol-5-yloxy]phenylacetic acid hydrochloride This product is taken up in dichloromethane (8 ml) and treated with a solution of hydrochloric acid in ether in the presence of a few drops of water. After 20 min, the beige crystals formed are isolated to give the compound 31 (472 mg; 96%).

Elemental analysis ($C_{18}H_{19}N_2O_3Cl$, 0.5 $H_2O$), % calculated: C 60.76; H 5.67; N 5.87; % found: C 60.63; H 5.65; N 7.48 $^1$H NMR, DMSO-d6 (ppm): 2.97 m, 4H; 5.82 s, 1H; 6.80 dd, 1H; 7.15–7.62 m, 8H; 8.06 s, 3H; 10.88 s, 1H; 13.06 broad s, 1H. Melting point: 178° C.

EXAMPLE 32

(±)-2-[3-(2-Aminoethyl)-1H-indol-5-yloxy]-2-phenylacetamide hydrochloride

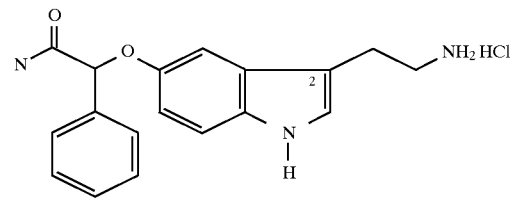

The compound 29A (600 mg; 1.41 mmol) in solution in ethanol (4 ml) in the presence of ammonium hydroxide (6 ml) and ammonium chloride (1 g), is heated at 65° C. for 17 hours. After this time, ammonium hydroxide (2 ml) and ammonium chloride (1 g) are again added and the mixture is heated for a further 20 hours.

The medium is then evaporated to dryness; the syrup is taken up in ethyl acetate and washed with water and then with a saturated sodium chloride solution. The organic phase is dried over sodium sulfate, filtered and evaporated to dryness. The syrup obtained is purified on a silica gel column, eluted with a dichloromethane/acetone mixture (10:1; v/v). The pure product is isolated in the form of a white foam (455 mg; 52%).

This product is then taken up in dichloromethane (6 ml) and treated with a solution of hydrochloric acid in ether in the presence of a few drops of water. After 20 min, the white crystals formed are isolated to give the com-pound 32 (271 mg; 76%).

Elemental analysis ($Cl_{18}H_{20}N_3O_2Cl$, 0.8 $H_2O$), % calculated: C 60.02; H 6.04; N 11.66; % found: C 60.10; H 5.83; N 11.42 $^1$H NMR, DMSO-d6 (ppm): 3.01 m, 4H; 5.66 s, 1H; 6.84 dd, 1H; 7.18–7.87 m, 8H; 8.09 s, 3H; 10.86 d, 1H. Melting point: 130° C.

EXAMPLE 33

Ethyl (±)-[3-(2-aminoethyl)-1H-indol-5-yloxy]phenylacetate hydrochloride

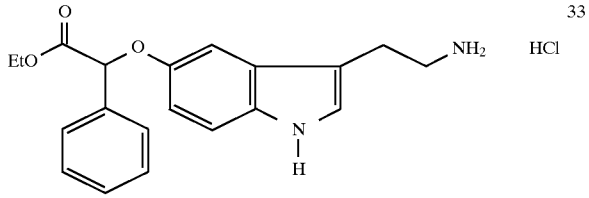

The compound 31A (200 mg; 0.487 mmol) in solution in ethanol (3 ml) is treated with a solution of hydrochloric acid in ether (excess). After stirring for 1 hour at room temperature, the mixture is evaporated to dryness and coevaporated twice with toluene (10 ml). The solid obtained is recrystallized from ethanol to give the compound 33 in the form of a white powder (120 mg; 71%).
Elemental analysis ($C_{20}H_{23}N_2O_3Cl$), % calculated: C 64.08; H 6.18; N 7.47; % found: C 63.68; H 6.14; N 7.42 $^1$H NMR. DMSO-d6 (ppm): 1.12 t, 3H; 2.96 m, 4H; 4.12 q, 2H; 5.93 s, 1H; 6.82 dd, 1H; 7.14–7.61 m, 8H; 7.99 s, 3H; 10.89 s, 1H. Melting point: 253° C.

EXAMPLE 34

Ethyl (±)-[3-(2-aminoethyl)-1H-indol-5-yloxy] phenylacetate hydrochloride and ethyl (–)-[3-(2-aminoethyl)-1H-indol-5-yloxy]phenylacetate hydrochloride

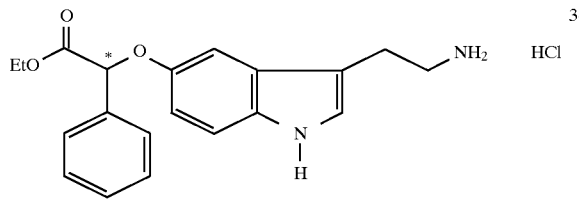

34

The separation of the two enantiomers of the compound 33 is carried out by derivatization of the compound 31A with (R)-(–)-2-phenylglycinol, separation of the diastereoisomers and formation of the pure enantiomeric esters.

To the compound 31A (1 g; 2.44 mmol) in solution in dichloromethane (2.4 ml), there are added successively PyBOP (1.40 g; 2.68 mmol), (R)-(–)-2-phenylglycinol (367 mg; 2.68 mmol) and diisopropylethylamine (0.64 ml; 3.66 mmol). The mixture is stirred at room temperature for 2 hours and then evaporated to dryness. The syrup obtained is taken up in dichloromethane, and washed with water; the organic phase is dried over sodium sulfate, filtered and evaporated to dryness.

The two diastereoisomers obtained are separated on a silica gel column, eluted with a dichloromethane/ethyl acetate mixture (4:1; v/v).

Each of the two products obtained is then solubilized in an ethanol/dioxane mixture (1:5; v/v) and treated with concentrated sulfuric acid (excess) at 100° C. for 1 hour.

The media are then evaporated to dryness, taken up in dichloromethane, washed with a saturated sodium bicarbonate solution and then with water. The organic phases are dried over sodium sulfate, filtered and evaporated to dryness.

The syrups obtained are purified on silica gel columns, eluted with a chloroform/methanol/ammonium hydroxide mixture (80:18.5:1.5; v/v).

The first pure product is isolated in the form of a colorless syrup which leads, after treatment with hydrochloric acid in ether, to the compound 34A (105 mg; 24%).
Elemental analysis ($C_{20}H_{23}N_2O_3Cl$), % calculated: C 64.08; H 6.18; N 7.47; % found: C 63.90; H 6.26; N 7.16 $^1$H NMR, DMSO-d6 (ppm): 1.11 t, 3H; 2.96 m, 4H; 4.11 m, 2H; 5.92 s, 1H; 6.86 dd, 1H; 7.14–7.60 m, 8H; 7.93 broad s, 3H; 10.89 s, 1H. Melting point: 200° C. Optical rotation: $[\alpha]_D$+ 62 (MeOH, c=0.1)

The second pure product is isolated in the form of a colorless syrup which leads, after treatment with hydrochloric acid in ether, to the compound 34B (51 mg; 12%).
Elemental analysis ($C_{20}H_{29}N_2O_3Cl$), % calculated: C 64.08; H 6.18; N 7.47; % found: C 63.20; H 6.24; N 7.13 $^1$H NMR, DMSO-d6 (ppm): 1.11 t, 3H; 2.97 m, 4H; 4.11 m, 2H; 5.92 s, 1H; 6.85 dd, 1H; 7.14–7.60 m, 8H; 8.06 s, 3H; 10.89 s, 1H. Melting point: 225° C. Optical rotation: $[\alpha]_D$–58° (MeOH; c=0.12)

EXAMPLE 35

Ethyl 5-[3-(1-methylpiperidin-4-yl)-1H-indol-5-yloxy]pentanoate hydrochloride

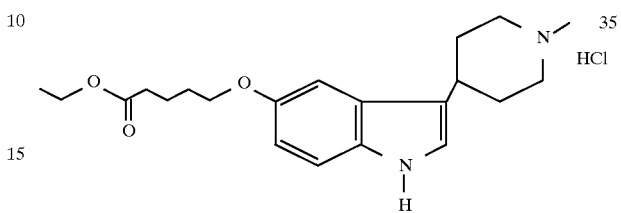

35

35A 3-(N-tert-Butoxycarbonyl-1,2,3,6-tetrahydropyridin-4-yl)-1H-indol-5-ol

To a solution of sodium (4.8 g; 210 mmol) in dry methanol (130 ml), there are added, at room temperature, 5-hydroxyindole (4 g; 30.04 mmol) and N-(tert-butoxycarbonyl)piperidone (8.9 g; 45.1 mmol).

The mixture is heated under reflux for 6 hours and then the solution is concentrated by evaporation under reduced pressure. The syrup obtained is taken up in dichloromethane, washed with a molar hydrochloric acid solution and then with water; the organic phase is dried over magnesium sulfate, filtered and evaporated to dryness. The syrup obtained is chromatographed on a silica gel column, eluted with a dichloromethane/acetone mixture (10:1; v/v) and then with dichloromethane/methanol (20;1; v/v). The pure product is isolated in the form of a pink powder (6.35 g; 67%).
$^1$H NMR, DMSO-d6 (ppm): 1.40 s, 9H; 2.46 m, 2H; 3.51 t, 2H; 3.99 m, 2H; 5.94 m, 1H; 6.58 dd, 1H; 7.10–7.29 m, 3H; 8.65 s, 1H; 10.84 s, 1H. Melting point: 224°–226° C.

35B -3 -(N-tert-Butoxycarbonylpiperidin-4-yl)-1H-indol-5-ol

The compound 35A (5 g; 15.9 mmol) in solution in methanol (100 ml) in the presence of a catalytic quantity of platinum oxide (4 spatulas) is hydrogenated at 40 psi in a Parr apparatus overnight.

The solution is then filtered on celite and evaporated to dryness. The syrup obtained is chromatographed on a silica gel column, eluted with a dichloromethane/acetone mixture (10:1; v/v). The pure product is isolated in the form of a colorless syrup crystallizing from ether to give a white powder (4.17 g; 83%).

Elemental analysis ($C_{18}H_{24}N_2O_3$), % calculated: C 68.33; H 7.65; N 8.85; % found: C 68.35; H 7.71; N 8.86 $^1$H NMR, DMSO-d6 (ppm): 1.40–1.54 m, 11H; 1.84 m, 2H; 2.79 m, 3H; 4.00 m, 2H; 6.53 dd, 1H; 6.81 d, 1H; 6.96 d, 1H; 7.07 d, 1H; 8.53 s, 1H; 10.45 s, 1H Melting point: 170° C.

35C 3-(1-Methylpiperidin-4-yl)-1H-indol-5-ol

The compound 35B (1 g; 3.16 mmol) in solution in anhydrous tetrahydrofuran (30 ml) is treated, under nitrogen and at room temperature, with a molar lithium aluminum hydride solution (6.3 ml; 6.32 mmol). The mixture is heated at 65° C. for 3 hours and then brought to 0° C. and treated with a sodium sulfate/water mixture. The paste formed is filtered on celite and the filtrate is evaporated to dryness to give a white powder (625 mg; 86%). This product is used without purification for the next stage.
$^1$H NMR, DMSO-d6 (ppm): 1.58–2.07 m, 6H; 2.21 s, 3H; 2.58 m, 1H; 2.83 d, 2H; 6.59 dd, 1H; 6.84 d, 1H; 6.96 d, 1H; 7.09 d, 1H; 8.55 s, 1H; 10.44 s, 1H.

35 Ethyl 5-[3-(1-methylpiperidin-4-yl)-1H-indol-5-yloxy]pentanoate hydrochloride The compound 35C (120 mg; 0.52 mmol) in solution in dry dimethylformamide (3 ml) is treated with cesium carbonate (255 mg; 0.78 mmol) at room temperature for 15 minutes. Ethyl 5-bromovalerate (100 μl; 0.62 mmol) is then added and the mixture is stirred at room temperature for 4 hours. The medium is diluted with ethyl acetate and washed with water and then with a saturated sodium chloride solution.

The organic phase is dried over sodium sulfate, filtered and evaporated to dryness. The syrup obtained is chromatographed on a silica gel column, eluted with a dichloromethane/methanol/ammonium hydroxide mixture (85:14:1; v/v). The pure product is obtained in the form of a yellow solid which leads after treatment with hydrochloric acid in ether, to the compound 35 (98 mg; 48).

Elemental analysis ($C_{21}H_{31}N_2O_3Cl$, 1.5 $H_2O$), a calculated: C 59.78; H 8.12; N 6.64; Cl 8.40; % found: C 59.98; H 7.88; N 6.43; Cl 9.00. $^1$H NMR, DMSO-d6 (ppm): 1.18 t, 3H; 1.72 broad s, 4H; 2.08 broad s, 4H; 2.38 t, 2H; 2.78 s, 3H; 3.09 m, 3H; 3.45 m, 2H; 3.99–4.11 m, 4H; 6.71 dd, 1H; 7.09–7.26 m, 3H; 10.44 s, 1H; 10.74 s, 1H.

EXAMPLE 36

Ethyl 5-(3-amino-1,2,3,4-tetrahydrocarbazole-6-yloxy)pentanoate hydrochloride

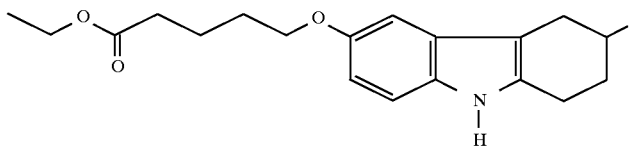

3-Amino-1,2,3,4-tetrahydro-6-hydroxycarbazole N-phthalimide (reference: G. E. A. COOMBES et al. J. Chem. Soc., No. 2, 1970, 325–326) (1 g; 3.01 mmol) in solution in dimethylformamide (6 ml) in the presence of cesium carbonate (1.47 g; 4.5 mmol) is treated with ethyl 5-bromovalerate (0.86 ml; 5.4 mmol) at 70° C. overnight.

The medium is diluted with ethyl acetate and washed with water and then with a saturated sodium chloride solution. The organic phase is dried over sodium sulfate, filtered and evaporated to dryness. The syrup obtained is chromatographed on a silica gel column, eluted with a dichloromethane/acetone mixture (100:1; v/v). The pure product is isolated in the form of a green syrup (850 mg; 61%).

This product (212 mg; 0.46 mmol) is deprotected by heating at 90° C. in ethylenediamine (3.3 ml) for 2 hours. The mixture is coevaporated 4 times with toluene and the orange-colored crystals obtained are then purified on a silica gel column, eluted with a dichloromethane/methanol/ammonium hydroxide mixture (90:9:1; v/v). The pure product is isolated in the form of yellow crystals which lead, after treatment with hydrochloric acid in ether, to the compound 36 (241 mg; 66%).

Elemental analysis: ($C_{19}H_{27}N_2O_3Cl$, 0.7 $H_2O$), % calculated: C 60.13; H 7.54; N 7.38; % found: C 60.13; H 7.20; N 7.57. $^1$H NMR, DMSO-d6 (ppm): 1.16 t, 3H; 1.68 m, 4H; 1.91 m, 1H; 2.15 m, 1H; 2.35 t, 2H; 2.58–2.79 m, 3H; 3.03 dd, 1H; 3.44 m, 1H; 3.92 t, 2H; 4.02 q, 2H; 6.61 dd, 1H; 6.82 d, 1H; 7.10 d, 1H; .8.37 s, 3H; 10.66 s, 1H. Melting point: 114° C.

EXAMPLE 37

Ethyl (R)-5-[3-(N-methylpyrrolidin-2-yl-methyl)-1H-indol-5-yloxy]pentanoate hydrochloride.

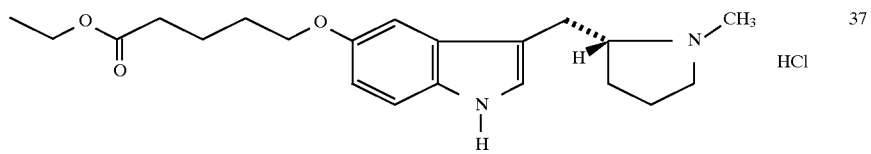

37A -(R)-5-hydroxy-3-(N-methylpyrrolidin-2-ylmethyl)-1H-indole (R)-5-Methoxy-3-(N-methylpyrrolidin-2-ylmethyl)-1H-indole (reference: J. E. Macor et al.: J. Med. Chem. 1992, 35, 4503–4505) (800 mg; 3.27 mmol) in solution in anhydrous dichloromethane (32 ml) is treated, under nitrogen and at −78° C., with a 1M boron tribromide solution (13 ml; 13.2 mmol). The mixture is stirred for 2 hours at −78° C. and then for one hour at room temperature and then brought to −78° C. to be treated with 4 ml of ethanol. The medium is evaporated to dryness and the syrup obtained is purified on a silica gel column, eluted with a dichloromethane/methanol/ammonium hydroxide mixture (85:14:1; v/v). The pure product is isolated in the form of a colorless syrup (429 mg; 57%).

$^1$H NMR, DMSO-d6 (ppm): 1.45–1.62 m, 4H; 2.03 m, 1H; 2.34–2.43 m, 5H; 2.92 m, 2H; 6.55 dd, 1H; 6.79 d, 1H; 7.01 d, 1H; 7.08 d, 1H; 8.56 s, 1H; 10.44 s, 1H. 37-Ethyl (R)-5-[3-(N-methylpyrrolidin-2-ylmethyl)-1H-indol-5-yloxy]pentanoate hydrochloride.

The compound 37A (250 mg; 1.08 mmol) in solution in dimethylformamide (2 ml) in the presence of cesium carbonate (528 mg; 1.62 mmol) is treated with ethyl 5-bromovalerate (0.31 ml; 1.9 mmol) at 60° C. overnight.

The mixture is filtered on celite and evaporated to dryness. The syrup obtained is chromatographed on a silica gel column, eluted with a dichloromethane/methanol/ammonium hydroxide mixture (85:14:1; v/v). The pure product leads, after treatment with hydrochloric acid in ether, to the compound 37 (216 mg; 53%).

EXAMPLE 38

5-[3-(2-{N-2-Methoxyethyl}ethyl)-1H-indol-5-yloxy]-N-ethylpentanamide hydrochloride.

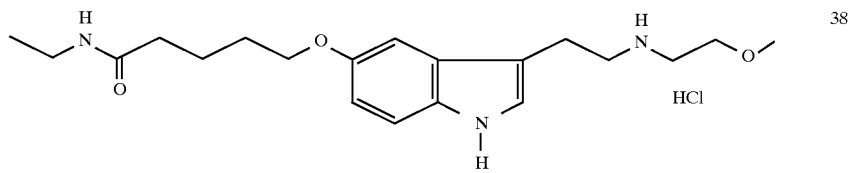

38

The compound 25 (200 mg; 0.66 mmol), in base form, in solution in anhydrous dichloromethane (4 ml) in the presence of triethylamine (0.138 ml; 0.99 mmol) is treated at 0° C. with 2-bromomethoxyethane (68 μl; 0.73 mmol). The mixture is then stirred at room temperature for 2 hours. The medium is diluted with dichloromethane, washed with water and then with a saturated sodium chloride solution. The organic phase is dried over sodium sulfate, filtered and evaporated to dryness. The syrup obtained is purified on a silica gel column, eluted with a dichloromethane/methanol/ammonium hydroxide mixture (85:14:1; v/v). The monoalkylation product is separated from the dialkylation product and leads, after treatment with hydrochloric acid in ether, to the compound 38 (60 mg; 25%).

EXAMPLE 39

N-{6-[3-(2-N-Methylaminoethyl)-1H-indol-5-yloxy]hexyl}methanesulfonamide hydrochloride

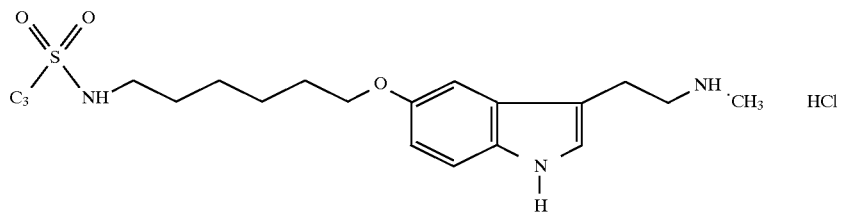

39

The product 19 in its protected form (-NHBOC) (300 mg; 0.66 mmol) in solution in anhydrous tetrahydrofuran (5 ml) is treated at room temperature with a (1M) solution of lithium aluminum hydride in THF (2.64 ml; 2.64 mmol). The mixture is heated at 50° C. for 4 hours and then brought to room temperature and neutralized by addition of a sodium sulfate/water mixture. The medium is filtered on celite and the filtrate is evaporated to dryness. The syrup obtained is chromatographed on a silica gel column, eluted with a dichloromethane/methanol/ammonium hydroxide mixture (80:18.5:1.5; v/v). The pure product is isolated in the form of a syrup which leads, after treatment with hydrochloric acid in ether, to the compound 39 (93 mg; 35%).

EXAMPLE 40

N-{6-[3-(2-N-Dimethylaminoethyl)-1H-indol-5-yloxy]hexylmethanesulfonamide hydrochloride To the product 19 (1.08 g; 3.05 mmol) in solution in methanol (43 ml) at −4° C. in the presence of sodium cyanoborohydride (384 mg; 6.11 mmol) and glacial acetic acid (0.87 ml; 15.2 mmol) there is added dropwise and over 10 minutes formaldehyde (38% in water) (0.60 ml; 7.64 mmol). After stirring for 20 minutes at 0° C. and 1 h 20 min at room temperature, a saturated potassium carbonate solution is added and then the mixture is evaporated to dryness. The syrup is taken up in dichloromethane and washed with water. The organic phase is dried over sodium sulfate, filtered and evaporated to dryness. The syrup obtained is chromatographed on a silica gel column, eluted with a dichloromethane/methanol/ammonium hydroxide mixture (90:9.5:0.5; v/v). The pure product is isolated in the form of a colorless syrup which leads, after treatment with hydrochloric acid in ether, to the compound 40 in the form of a white powder (880 mg; 69%).

Elemental analysis ($C_{19}H_{32}N_3O_35Cl$, 0.2 EtOH): % calculated: C=54.54; H=7.83; N=9.84; Cl=8.30 % found: C=54.73; H=7.84; N=9.67; Cl=8.40 $^1H$ NMR, DMSO-$d_6$ (ppm): 1.39–1.51 m, 6H; 1.68–1.75 m, 2H; 2.80 s, 6H; 2.86 s, 3H; 2.93 m, 2H; 3.06–3.10 m, 2H; 3.22–3.29 m, 2H; 3.96 t, 2H; 6.72 dd, 1H; 6.97 t, 1H; 7.14 dd, 2H; 7.22 d, 1H; 10.62 broad s, 1H; 10.81 s, 1H Melting point: 160° C.

EXAMPLE 41

(R)-N-{6-[3-(1-Methylpyrrolidin-2-ylmethyl)-1H-indol-5-yloxyhexyl]methanesulfonamide hydrochloride

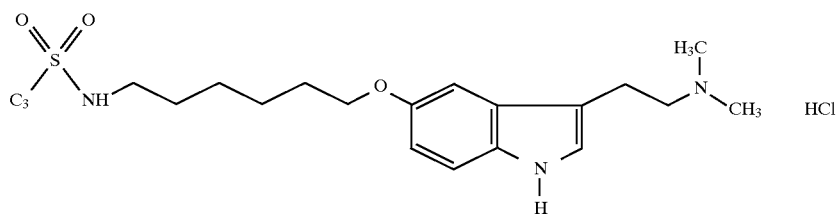

40

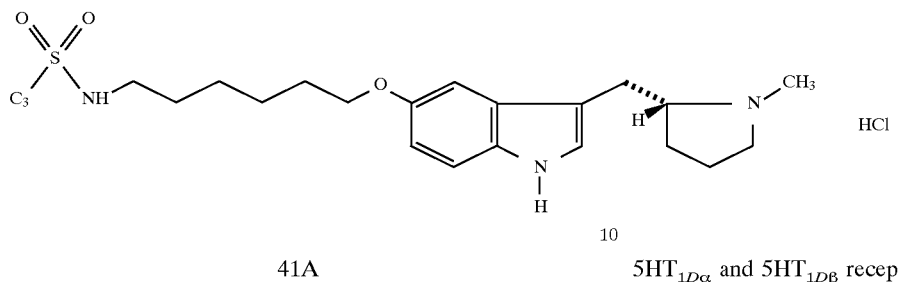

41

41A (R)-6-[3-(1-Methylpyrrolidin-2-ylmethyl)-1H-indol-5-yloxy]hexanenitrile

The compound 41A is prepared from the compound 37A (500 mg; 2.16 mmol) and 6-bromocapronitrile (685 mg; 3.89 mmol) according to the method described for the preparation of Example 37.

The syrup obtained is chromatographed on a silica gel column, eluted with a dichloromethane/methanol/ammonium hydroxide mixture (85:14:1; v/v). The pure product is isolated in the form of a syrup (456 mg; 65%).

41B (R)-6-[3-(1-Methylpyrrolidin-2-ylmethyl)-1H-indol-5-yloxy]hexylamine

The compound 41B is prepared from the compound 41A (450 mg; 1.38 mmol) according to the method described for the preparation of Example 18A. The crude product obtained (440 mg; 97%) is used directly in the next stage.

41

(R)-N-{6-[3-(1-Methylpyrrolidin-2-ylmethyl)-1H-indol-5-yloxyhexyl]methanesulfonamide hydrochloride The compound 41 is prepared from the amine 41B (440 mg; 1.34 mmol) and mesyl chloride (124 μl; 1.6 mmol) according to the method described for the preparation of Example 19. The syrup obtained is chromatographed on a silica gel column, eluted with a dichloromethane/methanol/ammonium hydroxide mixture (85:14:1; v/v). The pure product is isolated in the form of a syrup which leads, after treatment with hydrochloric acid in ether, to the compound 41 (392 mg; 72%)

BIOLOGICAL RESULTS

The human receptors $5HT_{1D\alpha}$ and $5HT_{1D\beta}$ were cloned based on the sequences published by M. Hamblin and M. Metcalf, Mol. Pharmacol., 40, 143 (1991) and Weinshenk et al., Proc. Natl. Acad. Sci. 89, 3630 (1992).

Transient transfection and stable transfection of genes for these receptors was carried out in Cos-7 and CHO-$K_1$ cell lines using an electroporator.

The HeLa HA7 cell line expressing the human $5HT_{1A}$ receptor was obtained from Tulco (Duke Univ., Durham, N.C., USA) and cultured according to the method of Fargin et al., J. Biol. Chem. 264, 14848 (1989).

The study of the binding of the derivatives of the present invention with the human $5HT_{1D\alpha}$, $5HT_{1D\beta}$ and $5HT_{1A}$ receptors was carried out according to the method described by P. Pauwels and C. Palmier (Neuropharmacology, 33, 67, 1994).

The incubation media for these binding measurements comprise 0.4 ml of cell membrane preparation, 0.05 ml of a tritiated ligand [[3H]-5CT (final concentration: 2 nM) for the $5HT_{1D\alpha}$ and $5HT_{1D\beta}$ receptors and [3H]-8OH-DPAT (final concentration: 1 nM) for the 5HT1A receptor] and 0.05 ml of the molecule to be tested (final concentrations: 0.1 to 1000 nM) or 10 μM (final concentration) of serotonin ($5HT_{1D\alpha}$ and $5HT_{1D\beta}$) or 1 μM (final concentration) of spiroxatrine (5HT1A).

Results obtained: the few examples which follow, chosen from the compounds of the present invention, illustrate the profile of the compounds of the present invention as regards their binding to the human $5HT_{1D}$ and $5HT_{1A}$ receptors:

|  | Ki (nM) | | |
| --- | --- | --- | --- |
| Examples | $5HT_{1D\alpha}$ | $5HT_{1D\beta}$ | $5HT_{1A}$ |
| 16 | 1.5 | 0.7 | 9 |
| 17 | 2.2 | 2.6 | 24.3 |
| 18 | 2.4 | 2 | 78.6 |
| 19 | 1.1 | 0.7 | 11.5 |
| 20 | 2 | 1.1 | 46.5 |
| 23 | 0.9 | 0.4 | 40 |
| Sumatriptan | 9 | 26 | 440 |
| Naratriptan | 1.6 | 2 | 46 |

The derivatives of the present invention are, in addition, capable, like serotonin, of inducing the contraction of the rabbit saphenous vein rings mediated by the "$5HT_{1-like}$" receptors.

The technique used was adapted from Van Heuven-Nolsen D. et al., Eur. J. Pharmacol. 191, 375–382 (1990) and from Martin G. R. and Mc Lennan S. J., Naunyn-Schmiedeberg's Arch. Pharmacol. 342, 111–119 (1990) and therefore makes it possible to determine a $pD_2$ value and an $E_{max}$ relative to serotonin for each product tested.

The few examples which follow, chosen from the compounds of the present invention, demonstrate their agonist profile in this model in comparison with sumatriptan and naratriptan.

| Contraction of the rabbit saphenous vein | | |
| --- | --- | --- |
| Examples | $pD_2$ | Relative $E_{max}$* |
| 12 | 6.16 | 0.8 |
| 13 | 6.51 | 1.2 |
| 16 | 6.62 | 1.36 |
| 19 | 7.8 | 1 |
| Sumatriptan | 5.75 | 1.26 |
| Naratriptan | 5.54 | 1 |

* review of the $E_{max}$ of the compounds mentioned to the $E_{max}$ of serotonin.

These biological results illustrate the value of the compounds of the present invention since, as the above examples show, they compare favorably with sumatriptan and with naratriptan as regards their binding to the human $5HT_{1D}$ receptors and their efficacy as agonists in the rabbit saphenous vein contraction model.

The aromatic ethers derived from indoles which form part of this invention are new compounds having a very high affinity and a very good selectivity for the receptors commonly called $5HT_{1\text{-}like}$ and more particularly for the receptors called $5HT_{1B}$ and $5HT_{1D}$, according to the new nomenclature recently proposed by P. Humphrey, P. Hartig and D. Hoyer (TIPS, 14, 233–236, 1993).

In human therapy, the compounds of the general formula (I) according to the invention are particularly useful for the treatment and prevention of disorders linked to serotonin at the level of the central nervous system and of the vascular system. These compounds can therefore be used in the treatment and prevention of depression, obsessive compulsive disorders, panic attacks, bulimia, anorexia, aggressiveness, alcoholism, addiction to smoking, hypertension, nausea, sexual dysfunction, antisocial behavior, anxiety, migraine, vascular facial pain and chronic vascular cephalalgia, spasticity, Parkinson's or Alzheimer's disease and memory disorders.

The present invention also relates to the medicaments consisting of at least one compound of formula (I) in the pure state or in the form of a composition in which it is combined with any other pharmaceutically compatible product, which may be inert or physiologically active. The medicaments according to the invention may be used via the oral, nasal, parenteral, rectal or topical route.

As solid compositions for oral administration, there may be used tablets, pills, powders (gelatin capsules, cachets) or granules. In these compositions, the active ingredient according to the invention is mixed with one or more inert diluents, such as starch, cellulose, sucrose, lactose or silica, under an argon stream. These compositions may also comprise substances other than diluents, for example one or more lubricants such as magnesium stearate or talc, a coloring, a coating (sugarcoated tablets) or a glaze.

As liquid compositions for oral administration, there may be used pharmaceutically acceptable solutions, suspensions, emulsions, syrups and elixirs containing inert diluents such as water, ethanol, glycerol, vegetable oils or paraffin oil.

These compositions may comprise substances other than diluents, for example wetting, sweetening, thickening, flavoring or stabilizing products.

The sterile compositions for parenteral administration may be preferably solutions which are aqueous or nonaqueous, suspensions or emulsions. As solvent or vehicle, there may be used water, propylene glycol, polyethylene glycol, vegetable oils, in particular olive oil, injectable organic esters, for example ethyl oleate or other suitable organic solvents. These compositions may also contain adjuvants, in particular wetting, isotonizing, emulsifying, dispersing and stabilizing agents. The sterilization may be carried out in several ways, for example by aseptizing filtration, by incorporating into the composition sterilizing agents, by irradiation or by heating. They may also be prepared in the form of sterile solid compositions which may be dissolved at the time of use in sterile water or any other injectable sterile medium.

The compositions for rectal administration are suppositories or rectal capsules which contain, in addition to the active product, excipients such as cocoa butter, semisynthetic glycerides or polyethylene glycols.

The compositions for topical administration may be for example creams, lotions, collyrea, collutoria, nasal drops or aerosols.

The doses depend on the desired effect, the duration of the treatment and the route of administration used; they are generally between 0.001 g and 1 g (preferably between 0.005 g and 0.25 g) per day, preferably via the oral route for an adult with unit doses ranging from 0.1 mg to 500 mg of active substance, preferably from 1 mg to 50 mg.

In general, the doctor will determine the appropriate dosage according to the age, the weight and all the other factors specific to the subject to be treated. The following examples illustrate compositions according to the invention [in these examples, the term "active component" designates one or more (generally one) of the compounds of formula (I) according to the present invention]:

Tablets

They may be prepared by direct compression or using an intermediate wet granulation. The direct compression procedure is preferred but it may not be suitable in all cases depending on the doses and the physical properties of the active component.

| A - By direct compression | |
|---|---|
| | mg per 1 tablet |
| Active component | 10.0 |
| Microcrystalline cellulose B.P.C. | 89.5 |
| Magnesium stearate | 0.5 |
| | 100.0 |

The active component is passed through a sieve with a mesh opening of 250 µm per side, mixed with the excipients and the mixture is compressed with the aid of 6.0 mm dies. Tablets exhibiting other mechanical resistances may be prepared by modifying the compression weight with the use of appropriate dies.

| B - Wet granulation | |
|---|---|
| | mg per one tablet |
| Active component | 10.0 |
| Lactose Codex | 74.5 |
| Starch Codex | 10.0 |
| Pregelatinized maize starch Codex | 5.0 |
| Magnesium stearate | 0.5 |
| Compression weight | 100.0 |

The active component is passed through a sieve with a mesh opening of 250 µm and mixed with lactose, starch and pregelatinized starch. The mixed powders are moistened with purified water, converted to the granule state, dried, sieved and mixed with magnesium stearate. The lubricated granules are tableted as for the direct compression formulas. A coating film may be applied to the tablets by means of appropriate film-forming materials, for example methylcellulose or hydroxypropyl-methylcellulose, according to conventional techniques. The tablets may also be coated with sugar.

| Capsules | |
|---|---|
| | mg per one capsule |
| Active component | 10.0 |
| * Starch 1500 | 89.5 |
| Magnesium stearate Codex | 0.5 |
| Filling weight | 100.0 |

* a form of starch which is directly compressible, obtained from the company Colorcon Ltd, Orpington, Kent, United Kingdom.

The active component is passed through a sieve with a mesh opening of 250 µm and mixed with the other substances. The mixture is introduced into hard gelatin capsules No. 2 on an appropriate filling machine. Other dosage units may be prepared by modifying the filling weight and, when necessary, by changing the size of the

| Syrup | |
|---|---|
| | mg per dose of 5 ml |
| Active component | 10.0 |
| Sucrose Codex | 2750.0 |
| Glycerin Codex | 500.0 |
| Buffer Flavoring Coloring Preservative | qs |
| Distilled water | 5.0 |

The active component, the buffer, the flavoring, the coloring and the preservative are dissolved in a portion of the water and the glycerin is added. The remainder of the water is heated to 80° C. and the sucrose is dissolved therein and then the solution is cooled. The two solutions are combined, the volume is adjusted and mixed. The syrup obtained is clarified by filtration.

| Suppositories | |
|---|---|
| Active component | 10.0 mg |
| *Witepsol H15 balance to | 1.0 g |

*Brand marketed for Adeps Solidus of the European Pharmacopoeia.

A suspension of the active component is prepared in Witepsol H15 and it is introduced into an appropriate machine with molds for 1 g suppositories.

| Liquid for administration by intravenous injection | |
|---|---|
| | g/l |
| Active component | 2.0 |
| Water for injection Codex balance to | 1000.0 |

Sodium chloride may be added to adjust the tonicity of the solution and to adjust the pH to the maximum stability and/or to facilitate the dissolution of the active component by means of an acid or a dilute alkali or by adding appropriate buffer salts. The solution is prepared, it is clarified and it is introduced into ampoules of appropriate size which are sealed by melting the glass. The liquid for injection may also be sterilized by heating in an autoclave according to one of the acceptable cycles. The solution may also be sterilized by filtration and introduced into a sterile ampoule under aseptic conditions. The solution may be introduced into the ampoules in a gaseous atmosphere.

| Cartridges for inhalation | |
|---|---|
| | g/cartridge |
| Micronized active component | 1.0 |
| Lactose Codex | 39.0 |

The active component is micronized in a fluid energy grinder and converted to the state of fine particles before mixing with lactose for tablets in a high energy mixer. The pulverulent mixture is introduced into hard gelatin capsules No. 3 on an appropriate encapsulating machine. The contents of the cartridges are administered with the aid of a powder inhaler.

| Pressurized aerosol with metering valve | | |
|---|---|---|
| | mg/dose | per 1 can |
| Micronized active component | 0.500 | 120 mg |
| Oleic acid Codex | 0.050 | 12 mg |
| Trifluoromethane for pharmaceutical use | 22.25 | 5.34 g |
| Dichlorodifluoromethane for pharmaceutical use | 60.90 | 14.62 g |

The active component is micronized in a fluid energy grinder and converted to the state of fine particles. The oleic acid is mixed with the trichlorofluoro-methane at a temperature of 10°–15° C. and the micronized medicament is introduced into the solution with the aid of a high-shear effect mixer. The suspension is introduced in a measured quantity into aluminum aerosol cans onto which appropriate metering valves delivering a dose of 85 mg of suspension are fitted; the dichlorodifluoro-methane is introduced into the cans by injection through the valves.

We claim:

1. A compound corresponding to general formula (I);

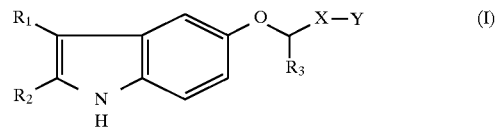

in which $R_1$ represents an amino residue corresponding to formula (i):

in which n represents an integer between 1 and 5, $R_4$ represents a hydrogen, a linear or branched alkyl group comprising from 1 to 6 carbon atoms or a $(CH_2)_m OR'$ group in which m represents an integer between 1 and 5, and R' is a linear or branched alkyl group comprising from 1 to 6 carbon atoms, $R_5$ represents a hydrogen, or a linear or branched alkyl group comprising from 1 to 6 carbon atoms, $R_2$ represents hydrogen, or $R_1$ and $R_2$, taken together, form a ring with 6 carbon atoms substituted with an amine functional group $(NR_4R_5)$ where $R_4$ and $R_5$ are as defined above, $R_3$ represents hydrogen, an alkyl residue comprising from 1 to 5 carbon atoms or an aromatic group, X may be omitted or may represent either a linear or branched alkyl chain comprising from 1 to 8 carbon atoms or an aromatic group or alternatively an arylalkyl group comprising from 1 to 10 carbon atoms which may be substituted at various positions with a linear or branched alkyl group comprising from 1 to 6 carbon atoms, an oxygen atom, an aryl group, a halogen atom, an alcohol group, an ether group, an ester group, a nitrile group, a nitro group, a ketone group, a thiol group, a thioether group, and an amine group, and Y represents $NHSO_2R'_6$, where $R'_6$ represents a linear or branched alkyl chain from 1 to 8 carbon atoms, a cycloalkyl from 4 to 10 carbon atoms, an aromatic residue which are variously substituted, and salts, hydrates, solvates, tacemates and bioprecursors thereof.

2. A compound of formula (I) according to claim 1, selected from the group consisting of:

N-{6-[3-(2-aminoethyl)-1H-indol-5-yloxy]hexyl}methanesulfonamide,

N-{6-[3-(2-N-Methyl aminoethyl-1H-indol-5-yloxy]hexyl}methanesulfonamide.

N-{6-[3-(2-N-Dimethylaminoethyl)-1H-indol-5-yloxy]hexyl}methanesulfonamide, and (R)-N-{6-[3-(1-Methylpyrrolidin-2-ylmethyl)-1H-indol-5-yloxy]hexyl}methanesulfonamide, their salts, hydrates, solvates and bioprecursors which are acceptable for therapeutic use.

3. A compound according to claim 1, characterized in that $R_1$ represents $R_4R_5N-CH_2-CH_2-$.

4. A compound according to claim 1, characterized in that $R_4$ and $R_5$ each represent a hydrogen or a methyl.

5. A compound according to claim 1, characterized in that $R_2$ represents a hydrogen.

6. A compound according to claim 1, characterized in that X represents a linear or branched alkyl chain comprising from 1 to 8 carbon atoms.

7. A compound according to claim 1, characterized in that X represents a phenyl onto which the Y substituent is attached at the para position.

8. A compound of claim 1, wherein $R'_6$ represents phenyl, benzyl or phenethyl which is variously substituted.

9. The compound of claim 1, wherein the compound of formula (I) comprises 1 or more asymmetric centers having isomeric forms.

10. The compound of claim 1, wherein the compound of formula (I) is a racemate of said compound.

11. The compound of claim 1, wherein the compound of formula (I) is an enantiomer of said compound.

12. The compound of claim 1, wherein the aromatic group of $R_3$ is a substituted phenyl group.

13. The compound of claim 1, wherein X is a phenyl group or a heterocycle group.

14. A compound according to claim 1, in the form of a salt acceptable for therapeutic use, characterized in that the salt is selected from the group consisting of a hydrochloride, hydrobromide, sulfate, methanesulfonate, fumarate, maleate and succinate.

15. A process for preparing a compound of formula (I) according to claim 1, comprising the step of condensing an intermediate of general formula (II):

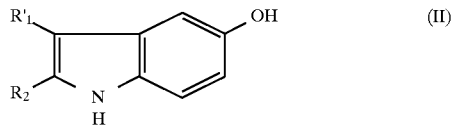

in which $R_2$ is defined as in claim 1 and $R'_1$ may be equivalent to $R_1$ or to a precursor of $R_1$, with a derivative of general formula (III):

in which X, Y and $R_3$ are defined as in claim 1 and L represents a leaving group.

16. The process of claim 15, further comprising the step of restoring the precursor of $R_1$ to $R_1$.

17. The process of claim 16, wherein the restoring step comprises cleaving a protective group from the precursor of $R_1$.

18. The process according to claim 15, wherein the leaving group is a halogen atom, a mesylate group, a tosylate group or a sulfate group.

19. The process according to claim 18, wherein the halogen atom is an iodine atom, a bromine atom or a chlorine atom.

20. A process for the preparation of a compound of formula (I), comprising the step of converting a compound of general formula (I) or a salt or a derivative comprising a group for protecting such a compound, to another compound of general formula (I).

21. A pharmaceutical composition containing, as an active ingredient, a compound according to claim 1, in combination with an acceptable pharmaceutical vehicle as a medicament.

22. A process for treating disorders relating to serotonin in a human comprising the step of administering to the human an effective amount of a compound of claim 1.

23. A process for treating migrane, vascular facial pain and chronic vascular cephalagia in a human the process comprising the step of administering to a human an effective amount of a compound of claim 1.

24. A process for treating depression, obsessive compulsive disorders, anxiety and panic attacks in humans comprising the step of administering to a human an effective amount of a compound of claim 1.

25. A process for treating schizophrenia, spasticity, aggressiveness, alcoholism, antisocial behavior, dietary disorders or sexual dysfunctions in humans, the process comprising the step of administering to a human an effective amount of a compound of claim 1.

26. A process for treating neurodegenertive diseases in humans, the process comprising the step of administering to a human an effective amount of a compound of claim 1.

27. The process of claim 25, wherein the dietary disorders are bulimia or anorexia.

28. The process of claim 26, wherein the neurodegenerative diseases are Parkinson's disease or Alzheimer's disease.

* * * * *

UNITED STATES PATENT AND TRADEMARK OFFICE
CERTIFICATE OF CORRECTION

PATENT NO. : 5,852,049

DATED : December 22, 1998

INVENTOR(S): Perez, et al.

It is hereby certified that error appear(s) in the above-identified patent and that said Letters Patent is hereby corrected as shown below:

Column 7, Line 11, change "NH2" to --- $NH_2$ ---.
Column 7, Line 54, change "yloxymethyllbenzoate" to --- yloxymethyl]benzoate ---.
Column 9, Line 53, change "EAAMPLE" to --- EXAMPLE ---.
Column 18, Line 35, change "a" to --- % ---.
Column 20, Line 42, change "a" to --- % ---.
Column 22, Line 36, change "accord" to --- according ---.
Column 22, Line 43, delete --- 5 --- after "of".
Column 26, Line 45, change "com-pound" to --- compound ---.
Column 30, Line 48, after "1H ","37-Ethyl" should begin on Line 49 in front of "(R)-5-[3-(N-methylpyrrolidin-2-ylmethyl)-1H-indol-5-yloxy]pentanoate hydrochloride.".

Column 37, Line 3, after the second instance of "the", insert --- capsule ---.

Signed and Sealed this

Eighteenth Day of May, 1999

*Attest:*

*Attesting Officer*

Q. TODD DICKINSON

*Acting Commissioner of Patents and Trademarks*